United States Patent
Hinga et al.

(10) Patent No.: US 9,370,149 B2
(45) Date of Patent: Jun. 21, 2016

(54) METHODS AND COMPOSITIONS TO PRODUCE RICE RESISTANT TO ACCASE INHIBITORS

(75) Inventors: Melissa Hinga, League City, TX (US); Steven Griffin, Alvin, TX (US); Melissa Shannon Moon, Pearland, TX (US); Russell D. Rasmussen, League City, TX (US); Federico Cuevas, League City, TX (US)

(73) Assignee: Ricetec Aktiengesellschaft, Vaduz (LI)

( * ) Notice: Subject to any disclaimer, the term of this patent is extended or adjusted under 35 U.S.C. 154(b) by 679 days.

(21) Appl. No.: 13/554,675

(22) Filed: Jul. 20, 2012

(65) Prior Publication Data

US 2013/0023416 A1  Jan. 24, 2013

Related U.S. Application Data

(60) Provisional application No. 61/510,585, filed on Jul. 22, 2011, provisional application No. 61/541,832, filed on Sep. 30, 2011.

(51) Int. Cl.
*C12N 15/82* (2006.01)
*A01H 1/06* (2006.01)
(Continued)

(52) U.S. Cl.
CPC *A01H 5/10* (2013.01); *A01N 37/46* (2013.01); *C12N 9/93* (2013.01); *C12N 15/8274* (2013.01); *C12Y 604/01002* (2013.01)

(58) Field of Classification Search
CPC ........... A01H 5/10; C12N 15/82; A01N 37/46
USPC ........... 800/260, 278, 300; 504/235; 435/418, 435/193; 536/23.2
See application file for complete search history.

(56) References Cited

U.S. PATENT DOCUMENTS

| 4,443,971 A | 4/1984 | Chaleff |
| 5,290,696 A | 3/1994 | Somers et al. |

(Continued)

FOREIGN PATENT DOCUMENTS

| EP | 2453012 | 5/2012 |
| WO | WO 95/29246 | 11/1995 |

(Continued)

OTHER PUBLICATIONS

Ouyang, et al., Jan. 1, 2007, Nucleic Acid Research 35 Database Issue: D846-851.*

(Continued)

*Primary Examiner* — Russell Kallis
*Assistant Examiner* — Weihua Weihua
(74) *Attorney, Agent, or Firm* — Barnes & Thornburg LLP; Alice O. Martin

(57) ABSTRACT

Mutant rice resistant/tolerant to ACCase inhibiting herbicides, in particular FOP herbicides, are listed in Table 1. The ACCase inhibiting herbicides used for selection include quizalofop. An exemplary mutant rice tolerant to an ACCase herbicide is disclosed, with a rice genome having G2096S or the equivalent, in the carboxyl transferase domain of the ACCase coding gene, using the Black-Grass numbering system. This mutation shows differential response to FOPs vs. DIMs herbicides, and a greater differential with comparable non-resistant rice lines. Methods to control weeds and methods to produce herbicide resistant rice including transgenic rice, are disclosed.

4 Claims, 10 Drawing Sheets

(51) Int. Cl.
*A01H 5/10* (2006.01)
*C12N 9/00* (2006.01)
*A01N 37/46* (2006.01)

(56) References Cited

U.S. PATENT DOCUMENTS

| | | | |
|---|---|---|---|
| 5,428,001 A | 6/1995 | Somers et al. | |
| 5,539,092 A | 7/1996 | Haselkorn et al. | |
| 5,736,629 A * | 4/1998 | Croughan | 800/300 |
| 5,756,290 A | 5/1998 | Haselkorn et al. | |
| 5,767,373 A | 6/1998 | Ward et al. | |
| 5,792,627 A | 8/1998 | Haselkorn et al. | |
| 5,801,233 A | 9/1998 | Haselkorn et al. | |
| 5,910,626 A | 6/1999 | Haselkorn et al. | |
| 5,939,602 A | 8/1999 | Volrath et al. | |
| 5,972,644 A | 10/1999 | Haselkorn et al. | |
| 6,066,779 A | 5/2000 | Yan | |
| 6,069,298 A * | 5/2000 | Gengenbach et al. | 800/278 |
| 6,084,155 A | 7/2000 | Volrath et al. | |
| 6,211,438 B1 | 4/2001 | Anderson et al. | |
| 6,211,439 B1 | 4/2001 | Anderson et al. | |
| 6,222,100 B1 | 4/2001 | Anderson et al. | |
| 6,282,837 B1 | 9/2001 | Ward et al. | |
| 6,288,306 B1 | 9/2001 | Ward et al. | |
| 6,308,458 B1 | 10/2001 | Volrath et al. | |
| 6,399,342 B1 | 6/2002 | Haselkorn et al. | |
| 6,448,476 B1 | 9/2002 | Barry | |
| 6,455,688 B1 | 9/2002 | Slabas et al. | |
| 6,727,414 B2 | 4/2004 | Moldenhauer et al. | |
| 6,808,904 B2 | 10/2004 | Ward et al. | |
| 6,870,075 B1 | 3/2005 | Beetham et al. | |
| 6,911,589 B2 | 6/2005 | Johnson | |
| 6,943,280 B2 | 9/2005 | Croughan | |
| 6,953,881 B2 | 10/2005 | Tillman | |
| 6,956,154 B2 | 10/2005 | Xie | |
| 7,094,606 B2 | 8/2006 | Arntzen et al. | |
| 7,141,726 B2 | 11/2006 | Moldenhauer et al. | |
| 7,253,347 B2 | 8/2007 | Linscombe | |
| 7,301,083 B2 | 11/2007 | Sarreal et al. | |
| 7,304,223 B2 | 12/2007 | Sarreal et al. | |
| 7,345,221 B2 | 3/2008 | Croughan | |
| 7,351,891 B2 | 4/2008 | Sarreal et al. | |
| 7,351,892 B2 | 4/2008 | Sarreal et al. | |
| 7,351,893 B2 | 4/2008 | Sarreal et al. | |
| 7,399,905 B2 | 7/2008 | Croughan | |
| 7,429,697 B2 | 9/2008 | Moldenhauer et al. | |
| 7,485,784 B2 | 2/2009 | Sarreal et al. | |
| 7,579,531 B2 | 8/2009 | Jodari | |
| 7,612,269 B2 | 11/2009 | Jodari | |
| 7,622,661 B2 | 11/2009 | Johnson | |
| 7,642,434 B2 | 1/2010 | Moldenhauer | |
| 7,642,435 B2 | 1/2010 | Sarreal et al. | |
| 7,671,254 B2 | 3/2010 | Tranel et al. | |
| 7,687,690 B2 | 3/2010 | Johnson et al. | |
| 7,754,947 B2 | 7/2010 | Croughan | |
| 7,786,360 B2 | 8/2010 | Linscombe | |
| 7,803,991 B2 | 9/2010 | Daniell | |
| 7,820,883 B2 | 10/2010 | Walsh et al. | |
| 7,838,733 B2 | 11/2010 | Wright et al. | |
| 7,842,856 B2 | 11/2010 | Tranel et al. | |
| H2258 H | 6/2011 | Arnevik et al. | |
| 8,071,847 B2 | 12/2011 | Walsh et al. | |
| 8,088,979 B2 | 1/2012 | Walsh et al. | |
| 8,097,774 B2 | 1/2012 | Hawkes et al. | |
| 8,106,276 B2 | 1/2012 | Luo | |
| 8,134,058 B2 | 3/2012 | Moldenhauer | |
| 8,153,870 B2 | 4/2012 | Re et al. | |
| 8,268,622 B2 | 9/2012 | Gocal et al. | |
| 8,283,536 B1 | 10/2012 | Re et al. | |
| 8,283,537 B1 | 10/2012 | Re et al. | |
| 8,288,635 B2 | 10/2012 | Moldenhauer | |
| 8,449,917 B2 | 5/2013 | Dave et al. | |
| 8,598,080 B2 | 12/2013 | Linscombe | |
| 8,796,177 B2 | 8/2014 | Mann et al. | |
| 2004/0107465 A1 * | 6/2004 | Tillman et al. | 800/320.2 |
| 2008/0256668 A1 | 10/2008 | Beetham et al. | |
| 2008/0300139 A1 | 12/2008 | Zawierucha et al. | |
| 2009/0093366 A1 | 4/2009 | Wright et al. | |
| 2009/0165166 A1 | 6/2009 | Feng et al. | |
| 2009/0235395 A1 | 9/2009 | Arntzen et al. | |
| 2009/0240073 A1 | 9/2009 | Barry et al. | |
| 2010/0048405 A1 | 2/2010 | Raymer et al. | |
| 2010/0293628 A1 | 11/2010 | Tuinstra et al. | |
| 2011/0124503 A1 | 5/2011 | Wright et al. | |
| 2011/0214196 A1 | 9/2011 | Raymer et al. | |
| 2012/0284812 A1 | 11/2012 | Mankin et al. | |
| 2012/0284853 A1 | 11/2012 | Mankin et al. | |
| 2013/0019349 A1 | 1/2013 | Gocal et al. | |
| 2013/0111618 A1 | 5/2013 | Mankin et al. | |
| 2014/0024530 A1 | 1/2014 | Poree et al. | |
| 2014/0045686 A1 | 2/2014 | Mankin et al. | |
| 2014/0250543 A1 | 9/2014 | Ostlie et al. | |
| 2014/0274710 A1 | 9/2014 | Mann et al. | |

FOREIGN PATENT DOCUMENTS

| | | | | |
|---|---|---|---|---|
| WO | WO2009/034188 | * | 3/2009 | C12N 15/82 |
| WO | WO 2010/040485 | | 4/2010 | |
| WO | WO 2010/046437 | | 4/2010 | |
| WO | WO2011/028833 | * | 9/2010 | A01H 5/00 |
| WO | WO 2011/028832 | | 3/2011 | |
| WO | WO2011/028833 | * | 3/2011 | C12N 15/82 |
| WO | WO 2011/028836 | | 3/2011 | |
| WO | WO 2013/016210 | | 1/2013 | |

OTHER PUBLICATIONS

Guo et al, 2004, Proc. Natl. Acad. Sci. USA 101: 9205-9210.*
Délye, et al. 2005, Plant Physiology 137.3: 794-806.*
International Search Report & Written Opinion of PCT/US12/47644 dated Oct. 29, 2012.
Délye et al., "An Isoleucine Residue within the Carboxyl-Transferase Domain of Multidomain Acetyl-Coenzyme A Carboxylase Is a Major Determinant of Sensitivity to Aryloxyphenoxypropionate But Not to Cyclohexanedione Inhibitors," *Plant Physiology*, 132: 1716-1723 (2003).
Délye et al., "Molecular Bases for Sensitivity to Acetyl-Coenzyme A Carboxylase Inhibitors in Black-Grass," *Plant Physiology*, 137: 794-806 (2005).
Liu et al., "Single-Site Mutations in the Carboxyltransferase Domain of Plastid Acetyl-CoA Carboxylase Confer Resistance to Grass-Specific Herbicides," *PNAS*, 104(9): 3627-3632 (2007).
Zhu et al., "Computational Simulations of the Interactions between Acetyl-Coenzyme-A Carboxylase and Clodinafop: Resistance Mechanism Due to Active and Nonactive Site Mutations," *J. Chem. Inf. Model*, 49(8): 1936-1943 (2009).
Search Report and Written Opinion issued in App. No. PCT/US2012/047644 (2012).
Cruz-Hipolito et al., "Resistance mechanism to acetyl coenzyme A carboxylase inhibiting herbicides in Phalaris paradoxa collected in Mexican wheat fields," *Plant Soil*, 355:121-130 (2012).
Search Report and Written Opinion issued in Int'l App. No. PCT/EP2014/067895 (2014).
Abe et al., "Genome sequencing reveals agronomically important loci in rice using MutMap," *Nat. Biotech.*, 30, 174-178 (2012).
Délye et al, "Universal' primers for PCR-sequencing of grass chloroplastic acetyl-CoA carboxylase domains involved in resistance to herbicides," *Weed Research*, 45:323-330 (2005).
Jain, "Tissue culture-derived variation in crop improvement," *Euphytica*, 118:153-166 (2001).
Rutger et al., "Registration of nine indica germplasms of rice," *Crop Sci.*, 45:1170-1171 (2005).
Suzuki et al., "MNU-induced mutant pools and high performance TILLING enable finding of any gene mutation in rice," *Mol. Genet. Genomics*, 279:213-223 (2008).
Martins et al., "Alleles Contributing to ACCase-Resistance in an Italian Ryegrass (*Lolium perenne* ssp. *multiflorum*) Population from Oregon," *Weed Science*, 62:468-473 (2014).
Matringe et al., "p-Hydroxyphenylpyruvate dioxygenase inhibitor-resistant plants," *Pest. Manage. Sci.*, 61:269-276 (2005).

(56) References Cited

OTHER PUBLICATIONS

Ruiz-Santaella et al., Detection of a new mutation of glycine to serine in the ACCase of a resistant biotype of *Phalaris paradoxa*. In: *Annual Meeting of the Weed Science Society of America,* Abstracts, New York: WSSA, 46:93 (2006).

Ostlie et al., "Development and characterization of mutant winter wheat (*Triticum aestivum* L.) accessions resistant to the herbicide quizalofop," *Theor. Appl. Genet.,* 128:343-351 (2015).

Okuzaki et al., "Chimeric RNA/DNA oligonucleotide-directed gene targeting in rice," Plant Cell Rep., 22:509-512 (2004).

* cited by examiner

```
NIPPONBARE.TXT    CCTGTTCTGCTAGGAATAATAGAACTACATACTGCTATGATTTTCCACTGGTGAGTTGAC
R0146.TXT         CCTGTTCTGCTAGGAATAATAGAACTACATACTGCTATGATTTTCCACTGGTGAGTTGAC
09PM72399.TXT     CCTGTTCTGCTAGGAATAATAGAACTACATACTGCTATGATTTTCCACTGGTGAGTTGAC

NIPPONBARE.TXT    TGCTCCCTTATATTCAATGCATTACCATAGCAAATTCATATTCGTTCATGTTGTCAAAAT
R0146.TXT         TGCTCCCTTATATTCAATGCATTACCATAGCAAATTCATATTCGTTCATGTTGTCAAAAT
09PM72399.TXT     TGCTCCCTTATATTCAATGCATTACCATAGCAAATTCATATTCGTTCATGTTGTCAAAAT

NIPPONBARE.TXT    AAGCCGATGAAAATTCAAAACTGTAGGCATTTGAAACTGCAGTGAGGAAGTCATGGTCCT
R0146.TXT         AAGCCGATGAAAATTCAAAACTGTAGGCATTTGAAACTGCAGTGAGGAAGTCATGGTCCT
09PM72399.TXT     AAGCCGATGAAAATTCAAAACTGTAGGCATTTGAAACTGCAGTGAGGAAGTCATGGTCCT

NIPPONBARE.TXT    CTAGTACCTCTGGTGCTTCTAAAGGTGTTGAAAATGCCCAATGTTATGTTAAAGCTACAG
R0146.TXT         CTAGTACCTCTGGTGCTTCTAAAGGTGTTGAAAATGCCCAATGTTATGTTAAAGCTACAG
09PM72399.TXT     CTAGTACCTCTGGTGCTTCTAAAGGTGTTGAAAATGCCCAATGTTATGTTAAAGCTACAG

NIPPONBARE.TXT    AGTTGGTATTTGCGGACAAACATGGGTCATGGGGCACTCCTTTAGTTCAAATGGACCGGC
R0146.TXT         AGTTGGTATTTGCGGACAAACATGGGTCATGGGGCACTCCTTTAGTTCAAATGGACCGGC
09PM72399.TXT     AGTTGGTATTTGCGGACAAACATGGGTCATGGGGCACTCCTTTAGTTCAAATGGACCGGC

NIPPONBARE.TXT    CTGCTGGGCTCAATGACATTGGTATGGTAGCTTGGACCTTGAAGATGTCCACTCCTGAAT
R0146.TXT         CTGCTGGGCTCAATGACATTGGTATGGTAGCTTGGACCTTGAAGATGTCCACTCCTGAAT
09PM72399.TXT     CTGCTGGGCTCAATGACATTGGTATGGTAGCTTGGACCTTGAAGATGTCCACTCCTGAAT

NIPPONBARE.TXT    TTCCTAGTGGTAGGGAGATTATTGTTGTTGCAAATGATATTACGTTCAGAGCTGGATCAT
R0146.TXT         TTCCTAGTGGTAGGGAGATTATTGTTGTTGCAAATGATATTACGTTCAGAGCTGGATCAT
09PM72399.TXT     TTCCTAGTGGTAGGGAGATTATTGTTGTTGCAAATGATATTACGTTCAGAGCTGGATCAT

NIPPONBARE.TXT    TTGGCCCAAGGGAAGATGCATTTTTTGAAGCTGTTACCAACCTAGCCTGTGAGAAGAAAC
R0146.TXT         TTGGCCCAAGGGAAGATGCATTTTTTGAAGCTGTTACCAACCTAGCCTGTGAGAAGAAAC
09PM72399.TXT     TTGGCCCAAGGGAAGATGCATTTTTTGAAGCTGTTACCAACCTAGCCTGTGAGAAGAAAC

NIPPONBARE.TXT    TTCCTCTTATTTATTTGGCAGCAAATTCTGGTGCTCGAATTGGCATAGCAGATGAAGTGA
R0146.TXT         TTCCTCTTATTTATTTGGCAGCAAATTCTGGTGCTCGAATTGGCATAGCAGATGAAGTGA
09PM72399.TXT     TTCCTCTTATTTATTTGGCAGCAAATTCTGGTGCTCGAATTGGCATAGCAGATGAAGTGA

NIPPONBARE.TXT    AATCTTGCTTCCGTGTTGGGTGGTCTGATGATGGCAGCCCTGAACGTGGGTTTCAGTACA
R0146.TXT         AATCTTGCTTCCGTGTTGGGTGGTCTGATGATGGCAGCCCTGAACGTGGGTTTCAGTACA
09PM72399.TXT     AATCTTGCTTCCGTGTTGGGTGGTCTGATGATGGCAGCCCTGAACGTGGGTTTCAGTACA

NIPPONBARE.TXT    TTTATCTAAGCGAAGAAGACTATGCTCGTATTGGCACTTCTGTCATAGCACATAAGATGC
R0146.TXT         TTTATCTAAGCGAAGAAGACTATGCTCGTATTGGCACTTCTGTCATAGCACATAAGATGC
09PM72399.TXT     TTTATCTAAGCGAAGAAGACTATGCTCGTATTGGCACTTCTGTCATAGCACATAAGATGC

NIPPONBARE.TXT    AGCTAGACAGTGGTGAAATTAGGTGGGTTATTGATTCTGTTGTGGGCAAGGAAGATGGAC
R0146.TXT         AGCTAGACAGTGGTGAAATTAGGTGGGTTATTGATTCTGTTGTGGGCAAGGAAGATGGAC
09PM72399.TXT     AGCTAGACAGTGGTGAAATTAGGTGGGTTATTGATTCTGTTGTGGGCAAGGAAGATGGAC
```

FIG. 4

```
NIPPONBARE.TXT    TTGGTGTGGAGAATATACATGGAAGTGCTGCTATTGCCAGTGCTTATTCTAGGGCATATA
R0146.TXT         TTGGTGTGGAGAATATACATGGAAGTGCTGCTATTGCCAGTGCTTATTCTAGGGCATATA
09PM72399.TXT     TTGGTGTGGAGAATATACATGGAAGTGCTGCTATTGCCAGTGCTTATTCTAGGGCATATA

NIPPONBARE.TXT    AGGAGACATTTACACTTACATTTGTGACTGGAAGAACTGTTGGAATAGGAGCTTATCTTG
R0146.TXT         AGGAGACATTTACACTTACATTTGTGACTGGAAGAACTGTTGGAATAGGAGCTTATCTTG
09PM72399.TXT     AGGAGACATTTACACTTACATTTGTGACTGGAAGAACTGTTGGAATAGGAGCTTATCTTG

NIPPONBARE.TXT    CTCGACTTGGCATCCGGTGCATACAGCGTCTTGACCAGCCTATTATTCTTACAGGCTATT
R0146.TXT         CTCGACTTGGCATCCGGTGCATACAGCGTCTTGACCAGCCTATTATTCTTACAGGCTATT
09PM72399.TXT     CTCGACTTGGCATCCGGTGCATACAGCGTCTTGACCAGCCTATTATTCTTACAGGCTATT

NIPPONBARE.TXT    CTGCACTGAACAAGCTTCTTGGGCGGGAAGTGTACAGCTCCCACATGCAGTTGGGTGGTC
R0146.TXT         CTGCACTGAACAAGCTTCTTGGGCGGGAAGTGTACAGCTCCCACATGCAGTTGGGTGGTC
09PM72399.TXT     CTGCACTGAACAAGCTTCTTGGGCGGGAAGTGTACAGCTCCCACATGCAGTTGGGTGGTC

NIPPONBARE.TXT    CCAAAATCATGGCAACTAATGGTGTTGTCCATCTTACTGTTTCAGATGACCTTGAAGGCG
R0146.TXT         CCAAAATCATGGCAACTAATGGTGTTGTCCATCTTACTGTTTCAGATGACCTTGAAGGCG
09PM72399.TXT     CCAAAATCATGGCAACTAATGGTGTTGTCCATCTTACTGTTTCAGATGACCTTGAAGGCG

NIPPONBARE.TXT    TTTCTAATATATTGAGGTGGCTCAGTTATGTTCCTGCCTACATTGGTGGACCACTTCCAG
R0146.TXT         TTTCTAATATATTGAGGTGGCTCAGTTATGTTCCTGCCTACATTGGTGGACCACTTCCAG
09PM72399.TXT     TTTCTAATATATTGAGGTGGCTCAGTTATGTTCCTGCCTACATTGGTGGACCACTTCCAG

NIPPONBARE.TXT    TAACAACACCGTTGGACCCACCGGACAGACCTGTTGCATACATTCCTGAGAACTCGTGTG
R0146.TXT         TAACAACACCGTTGGACCCACCGGACAGACCTGTTGCATACATTCCTGAGAACTCGTGTG
09PM72399.TXT     TAACAACACCGTTGGACCCACCGGACAGACCTGTTGCATACATTCCTGAGAACTCGTGTG

NIPPONBARE.TXT    ATCCTCGAGCGGCTATCCGTGGTGTTGATGACAGCCAAGGGAAATGGTTAGGTGGTATGT
R0146.TXT         ATCCTCGAGCGGCTATCCGTGGTGTTGATGACAGCCAAGGGAAATGGTTAGGTGGTATGT
09PM72399.TXT     ATCCTCGAGCGGCTATCCGTGGTGTTGATGACAGCCAAGGGAAATGGTTAGGTGGTATGT

NIPPONBARE.TXT    TTGATAAAGACAGCTTTGTGGAAACATTTGAAGGTTGGGCTAAGACAGTGGTTACTGGCA
R0146.TXT         TTGATAAAGACAGCTTTGTGGAAACATTTGAAGGTTGGGCTAAGACAGTGGTTACTGGCA
09PM72399.TXT     TTGATAAAGACAGCTTTGTGGAAACATTTGAAGGTTGGGCTAAGACAGTGGTTACTGGCA

NIPPONBARE.TXT    GAGCAAAGCTTGGTGGAATTCCAGTGGGTGTGATAGCTGTGGAGACTCAGACCATGATGC
R0146.TXT         GAGCAAAGCTTGGTGGAATTCCAGTGGGTGTGATAGCTGTGGAGACTCAGACCATGATGC
09PM72399.TXT     GAGCAAAGCTTGGTGGAATTCCAGTGGGTGTGATAGCTGTGGAGACTCAGACCATGATGC

NIPPONBARE.TXT    AAACTATCCCTGCTGACCCTGGTCAGCTTGATTCCCGTGAGCAATCTGTTCCTCGTGCTG
R0146.TXT         AAACTATCCCTGCTGACCCTGGTCAGCTTGATTCCCGTGAGCAATCTGTTCCTCGTGCTG
09PM72399.TXT     AAACTATCCCTGCTGACCCTGGTCAGCTTGATTCCCGTGAGCAATCTGTTCCTCGTGCTG

NIPPONBARE.TXT    GACAAGTGTGGTTTCCAGATTCTGCAACCAAGACTGCGCAGGCATTGCTGGACTTCAACC
R0146.TXT         GACAAGTGTGGTTTCCAGATTCTGCAACCAAGACTGCGCAGGCATTGCTGGACTTCAACC
09PM72399.TXT     GACAAGTGTGGTTTCCAGATTCTGCAACCAAGACTGCGCAGGCATTGCTGGACTTCAACC
```

FIG. 4 (cont.)

```
NIPPONBARE.TXT    GTGAAGGATTACCTCTGTTCATCCTCGCTAACTGGAGAGGCTTCTCTGGTGGACAAAGAG
R0146.TXT         GTGAAGGATTACCTCTGTTCATCCTCGCTAACTGGAGAGGCTTCTCTGGTGGACAAAGAG
09PM72399.TXT     GTGAAGGATTACCTCTGTTCATCCTCGCTAACTGGAGAGGCTTCTCTGGTGGACAAAGAG

NIPPONBARE.TXT    ATCTTTTTGAAGGAATTCTTCAGGCTGGCTCGACTATTGTTGAGAACCTTAGGACATACA
R0146.TXT         ATCTTTTTGAAGGAATTCTTCAGGCTGGCTCGACTATTGTTGAGAACCTTAGGACATACA
09PM72399.TXT     ATCTTTTTGAAGGAATTCTTCAGGCTGGCTCGACTATTGTTGAGAACCTTAGGACATACA

NIPPONBARE.TXT    ATCAGCCTGCCTTTGTCTACATTCCCATGGCTGCAGAGCTACGAGGAGGGGCTTGGGTTG
R0146.TXT         ATCAGCCTGCCTTTGTCTACATTCCCATGGCTGCAGAGCTACGAGGAGGGGCTTGGGTTG
09PM72399.TXT     ATCAGCCTGCCTTTGTCTACATTCCCATGGCTGCAGAGCTACGAGGAGGGGCTTGGGTTG

NIPPONBARE.TXT    TGGTTGATAGCAAGATAAACCCAGACCGCATTGAGTGCTATGCTGAGAGGACTGCAAAA
R0146.TXT         TGGTTGATAGCAAGATAAACCCAGACCGCATTGAGTGCTATGCTGAGAGGACTGCAAAA
09PM72399.TXT     TGGTTGATAGCAAGATAAACCCAGACCGCATTGAGTGCTATGCTGAGAGGACTGCAAAA

NIPPONBARE.TXT    GCAATGTTCTGGAACCGCAAGGGTTAATTGAGATCAAGTTCAGGTCAGAGGAACTCCAGG
R0146.TXT         GCAATGTTCTGGAACCGCAAGGGTTAATTGAGATCAAGTTCAGGTCAGAGGAACTCCAGG
09PM72399.TXT     GCAATGTTCTGGAACCGCAAGGGTTAATTGAGATCAAGTTCAGGTCAGAGGAACTCCAGG

NIPPONBARE.TXT    ATTGCATGAGTCGGCTTGACCCAACATTAATTGATCTGAAAGCAAAACTCGAAGTAGCAA
R0146.TXT         ATTGCATGAGTCGGCTTGACCCAACATTAATTGATCTGAAAGCAAAACTCGAAGTAGCAA
09PM72399.TXT     ATTGCATGAGTCGGCTTGACCCAACATTAATTGATCTGAAAGCAAAACTCGAAGTAGCAA

NIPPONBARE.TXT    ATAAAAATGGAAGTGCTGACACAAAATCGCTTCAAGAAAATATAGAAGCTCGAACAAAAC
R0146.TXT         ATAAAAATGGAAGTGCTGACACAAAATCGCTTCAAGAAAATATAGAAGCTCGAACAAAAC
09PM72399.TXT     ATAAAAATGGAAGTGCTGACACAAAATCGCTTCAAGAAAATATAGAAGCTCGAACAAAAC

NIPPONBARE.TXT    AGTTGATGCCTCTATATACTCAGATTGCGATACGGTTTGCTGAATTGCATGATACATCCC
R0146.TXT         AGTTGATGCCTCTATATACTCAGATTGCGATACGGTTTGCTGAATTGCATGATACATCCC
09PM72399.TXT     AGTTGATGCCTCTATATACTCAGATTGCGATACGGTTTGCTGAATTGCATGATACATCCC

NIPPONBARE.TXT    TCAGAATGGCTGCGAAAGGTGTGATTAAGAAAGTTGTGGACTGGGAAGAATCACGATCTT
R0146.TXT         TCAGAATGGCTGCGAAAGGTGTGATTAAGAAAGTTGTGGACTGGGAAGAATCACGATCTT
09PM72399.TXT     TCAGAATGGCTGCGAAAGGTGTGATTAAGAAAGTTGTGGACTGGGAAGAATCACGATCTT

NIPPONBARE.TXT    TCTTCTATAAGAGATTACGGAGGAGGATCTCTGAGGATGTTCTTGCAAAAGAAATTAGAG
R0146.TXT         TCTTCTATAAGAGATTACGGAGGAGGATCTCTGAGGATGTTCTTGCAAAAGAAATTAGAG
09PM72399.TXT     TCTTCTATAAGAGATTACGGAGGAGGATCTCTGAGGATGTTCTTGCAAAAGAAATTAGAG

NIPPONBARE.TXT    CTGTAGCAGGTGAGCAGTTTTCCCACCAACCAGCAATCGAGCTGATCAAGAAATGGTATT
R0146.TXT         CTGTAGCAGGTGAGCAGTTTTCCCACCAACCAGCAATCGAGCTGATCAAGAAATGGTATT
09PM72399.TXT     CTGTAGCAGGTGAGCAGTTTTCCCACCAACCAGCAATCGAGCTGATCAAGAAATGGTATT

NIPPONBARE.TXT    CAGCTTCACATGCAGCTGAATGGGATGATGACGATGCTTTTGTTGCTTGGATGGATAACC
R0146.TXT         CAGCTTCACATGCAGCTGAATGGGATGATGACGATGCTTTTGTTGCTTGGATGGATAACC
09PM72399.TXT     CAGCTTCACATGCAGCTGAATGGGATGATGACGATGCTTTTGTTGCTTGGATGGATAACC
```

FIG. 4 (cont.)

```
NIPPONBARE.TXT    CTGAAAACTACAAGGATTATATTCAATATCTTAAGGCTCAAAGAGTATCCCAATCCCTCT
R0146.TXT         CTGAAAACTACAAGGATTATATTCAATATCTTAAGGCTCAAAGAGTATCCCAATCCCTCT
09PM72399.TXT     CTGAAAACTACAAGGATTATATTCAATATCTTAAGGCTCAAAGAGTATCCCAATCCCTCT

NIPPONBARE.TXT    CAAGTCTTTCAGATTCCAGCTCAGATTTGCAAGCCCTGCCACAGGGTCTTTCCATGTTAC
R0146.TXT         CAAGTCTTTCAGATTCCAGCTCAGATTTGCAAGCCCTGCCACAGGGTCTTTCCATGTTAC
09PM72399.TXT     CAAGTCTTTCAGATTCCAGCTCAGATTTGCAAGCCCTGCCACAGGGTCTTTCCATGTTAC

NIPPONBARE.TXT    TAGATAAGGTAATTAGCTTACTGATGCTTATATAAATTCTTTTTCATTACATATGGCTGG
R0146.TXT         TAGATAAGGTAATTAGCTTACTGATGCTTATATAAATTCTTTTTCATTACATATGGCTGG
09PM72399.TXT     TAGATAAGGTAATTAGCTTACTGATGCTTATATAAATTCTTTTTCATTACATATGGCTGG

NIPPONBARE.TXT    AGAACTATCTAATCAAATAATGATTATAATTCCAATCGTTCTTTTTATGCCATTATGATC
R0146.TXT         AGAACTATCTAATCAAATAATGATTATAATTCCAATCGTTCTTTTTATGCCATTATGATC
09PM72399.TXT     AGAACTATCTAATCAAATAATGATTATAATTCCAATCGTTCTTTTTATGCCATTATGATC

NIPPONBARE.TXT    TTCTGAAATTTCCTTCTTTGGACACTTATTCAGATGGATCCCTCTAGAAGAGCTCAACTT
R0146.TXT         TTCTGAAATTTCCTTCTTTGGACACTTATTCAGATGGATCCCTCTAGAAGAGCTCAACTT
09PM72399.TXT     TTCTGAAATTTCCTTCTTTGGACACTTATTCAGATGGATCCCTCTAGAAGAGCTCAACTT

NIPPONBARE.TXT    GTTGAAGAAATCAGGAAGGTCCTTGGTTGAATCATATGATG
R0146.TXT         GTTGAAGAAATCAGGAAGGTCCTTGGTTGAATCATATGATG
09PM72399.TXT     GTTGAAGAAATCAGGAAGGTCCTTGGTTGAATCATATGATG
```

FIG. 4 (cont.)

```
NIPP-PRO.TXT        MDRPAGLNDIGMVAWTLKMSTPEFPSGREIIVVANDITFRAGSFGPREDAFFEAVTNLAC
R0146-PRO.TXT       MDRPAGLNDIGMVAWTLKMSTPEFPSGREIIVVANDITFRAGSFGPREDAFFEAVTNLAC
09PM72399-PRO.TX    MDRPAGLNDIGMVAWTLKMSTPEFPSGREIIVVANDITFRAGSFGPREDAFFEAVTNLAC

NIPP-PRO.TXT        EKKLPLIYLAANSGARIGIADEVKSCFRVGWSDDGSPERGFQYIYLSEEDYARIGTSVIA
R0146-PRO.TXT       EKKLPLIYLAANSGARIGIADEVKSCFRVGWSDDGSPERGFQYIYLSEEDYARIGTSVIA
09PM72399-PRO.TX    EKKLPLIYLAANSGARIGIADEVKSCFRVGWSDDGSPERGFQYIYLSEEDYARIGTSVIA

NIPP-PRO.TXT        HKMQLDSGEIRWVIDSVVGKEDGLGVENIHGSAAIASAYSRAYKETFTLTFVTGRTVGIG
R0146-PRO.TXT       HKMQLDSGEIRWVIDSVVGKEDGLGVENIHGSAAIASAYSRAYKETFTLTFVTGRTVGIG
09PM72399-PRO.TX    HKMQLDSGEIRWVIDSVVGKEDGLGVENIHGSAAIASAYSRAYKETFTLTFVTGRTVGIG

NIPP-PRO.TXT        AYLARLGIRCIQRLDQPIILTGYSALNKLLGREVYSSHMQLGGPKIMATNGVVHLTVSDD
R0146-PRO.TXT       AYLARLGIRCIQRLDQPIILTGYSALNKLLGREVYSSHMQLGGPKIMATNGVVHLTVSDD
09PM72399-PRO.TX    AYLARLGIRCIQRLDQPIILTGYSALNKLLGREVYSSHMQLGGPKIMATNGVVHLTVSDD

NIPP-PRO.TXT        LEGVSNILRWLSYVPAYIGGPLPVTTPLDPPDRPVAYIPENSCDPRAAIRGVDDSQGKWL
R0146-PRO.TXT       LEGVSNILRWLSYVPAYIGGPLPVTTPLDPPDRPVAYIPENSCDPRAAIRGVDDSQGKWL
09PM72399-PRO.TX    LEGVSNILRWLSYVPAYIGGPLPVTTPLDPPDRPVAYIPENSCDPRAAIRGVDDSQGKWL

NIPP-PRO.TXT        GGMFDKDSFVETFEGWAKTVVTGRAKLGGIPVGVIAVETQTMMQTIPADPGQLDSREQSV
R0146-PRO.TXT       GGMFDKDSFVETFEGWAKTVVTGRAKLGGIPVGVIAVETQTMMQTIPADPGQLDSREQSV
09PM72399-PRO.TX    GGMFDKDSFVETFEGWAKTVVTGRAKLGGIPVGVIAVETQTMMQTIPADPGQLDSREQSV

NIPP-PRO.TXT        PRAGQVWFPDSATKTAQALLDFNREGLPLFILANWRGFSGGQRDLFEGILQAGSTIVENL
R0146-PRO.TXT       PRAGQVWFPDSATKTAQALLDFNREGLPLFILANWRGFSGGQRDLFEGILQAGSTIVENL
09PM72399-PRO.TX    PRAGQVWFPDSATKTAQALLDFNREGLPLFILANWRGFSGGQRDLFEGILQAGSTIVENL

NIPP-PRO.TXT        RTYNQPAFVYIPMAAELRGGAWVVVDSKINPDRIECYAERTAK NVLEPQGLIEIKFRSE
R0146-PRO.TXT       RTYNQPAFVYIPMAAELRGGAWVVVDSKINPDRIECYAERTAK NVLEPQGLIEIKFRSE
09PM72399-PRO.TX    RTYNQPAFVYIPMAAELRGGAWVVVDSKINPDRIECYAERTAK NVLEPQGLIEIKFRSE

NIPP-PRO.TXT        ELQDCMSRLDPTLIDLKAKLEVANKNGSADTKSLQENIEARTKQLMPLYTQIAIRFAELH
R0146-PRO.TXT       ELQDCMSRLDPTLIDLKAKLEVANKNGSADTKSLQENIEARTKQLMPLYTQIAIRFAELH
09PM72399-PRO.TX    ELQDCMSRLDPTLIDLKAKLEVANKNGSADTKSLQENIEARTKQLMPLYTQIAIRFAELH

NIPP-PRO.TXT        DISLRMAAKGVIKKVVDWEESRSFFYKRLRRRISEDVLAKEIRAVAGEQFSHQPAIELIK
R0146-PRO.TXT       DISLRMAAKGVIKKVVDWEESRSFFYKRLRRRISEDVLAKEIRAVAGEQFSHQPAIELIK
09PM72399-PRO.TX    DISLRMAAKGVIKKVVDWEESRSFFYKRLRRRISEDVLAKEIRAVAGEQFSHQPAIELIK

NIPP-PRO.TXT        KWYSASHAAEWDDDDAFVAWMDNPENYKDYIQYLKAQRVSQSLSSLSDSSSDLQALPQGL
R0146-PRO.TXT       KWYSASHAAEWDDDDAFVAWMDNPENYKDYIQYLKAQRVSQSLSSLSDSSSDLQALPQGL
09PM72399-PRO.TX    KWYSASHAAEWDDDDAFVAWMDNPENYKDYIQYLKAQRVSQSLSSLSDSSSDLQALPQGL

NIPP-PRO.TXT        SMLLDKVISLLMLI
R0146-PRO.TXT       SMLLDKVISLLMLI
09PM72399-PRO.TX    SMLLDKVISLLMLI
```

FIG. 5

```
   1 CCTGTTCTGC TAGGAATAAT AGAACTACAT ACTGCTATGA TTTTCCACTG
  51 GTGAGTTGAC TGCTCCCTTA TATTCAATGC ATTACCATAG CAAATTCATA
 101 TTCGTTCATG TTGTCAAAAT AAGCCGATGA AAATTCAAAA CTGTAGGCAT
 151 TTGAAACTGC AGTGAGGAAG TCATGGTCCT CTAGTACCTC TGGTGCTTCT
 201 AAAGGTGTTG AAAATGCCCA ATGTTATGTT AAAGCTACAG AGTTGGTATT
 251 TGCGGACAAA CATGGGTCAT GGGGCACTCC TTTAGTTCAA ATGGACCGGC
 301 CTGCTGGGCT CAATGACATT GGTATGGTAG CTTGGACCTT GAAGATGTCC
 351 ACTCCTGAAT TCCTAGTGG TAGGGAGATT ATTGTTGTTG CAAATGATAT
 401 TACGTTCAGA GCTGGATCAT TTGGCCCAAG GGAAGATGCA TTTTTTGAAG
 451 CTGTTACCAA CCTAGCCTGT GAGAAGAAAC TTCCTCTTAT TTATTTGGCA
 501 GCAAATTCTG GTGCTCGAAT TGGCATAGCA GATGAAGTGA AATCTTGCTT
 551 CCGTGTTGGG TGGTCTGATG ATGGCAGCCC TGAACGTGGG TTTCAGTACA
 601 TTTATCTAAG CGAAGAAGAC TATGCTCGTA TTGGCACTTC TGTCATAGCA
 651 CATAAGATGC AGCTAGACAG TGGTGAAATT AGGTGGGTTA TTGATTCTGT
 701 TGTGGGCAAG GAAGATGGAC TTGGTGTGGA GAATATACAT GGAAGTGCTG
 751 CTATTGCCAG TGCTTATTCT AGGGCATATA AGGAGACATT TACACTTACA
 801 TTTGTGACTG GAAGAACTGT TGGAATAGGA GCTTATCTTG CTCGACTTGG
 851 CATCCGGTGC ATACAGCGTC TTGACCAGCC TATTATTCTT ACAGGCTATT
 901 CTGCACTGAA CAAGCTTCTT GGGCGGGAAG TGTACAGCTC CCACATGCAG
 951 TTGGGTGGTC CCAAAATCAT GGCAACTAAT GGTGTTGTCC ATCTTACTGT
1001 TTCAGATGAC CTTGAAGGCG TTTCTAATAT ATTGAGGTGG CTCAGTTATG
1051 TTCCTGCCTA CATTGGTGGA CCACTTCCAG TAACAACACC GTTGGACCCA
1101 CCGGACAGAC CTGTTGCATA CATTCCTGAG AACTCGTGTG ATCCTCGAGC
1151 GGCTATCCGT GGTGTTGATG ACAGCCAAGG GAAATGGTTA GGTGGTATGT
1201 TTGATAAAGA CAGCTTTGTG GAAACATTTG AAGGTTGGGC TAAGACAGTG
1251 GTTACTGGCA GAGCAAAGCT TGGTGGAATT CCAGTGGGTG TGATAGCTGT
1301 GGAGACTCAG ACCATGATGC AAACTATCCC TGCTGACCCT GGTCAGCTTG
1351 ATTCCCGTGA GCAATCTGTT CCTCGTGCTG ACAAGTGTG GTTTCCAGAT
1401 TCTGCAACCA AGACTGCGCA GGCATTGCTG GACTTCAACC GTGAAGGATT
1451 ACCTCTGTTC ATCCTCGCTA ACTGGAGAGG CTTCTCTGGT GGACAAAGAG
1501 ATCTTTTTGA AGGAATTCTT CAGGCTGGCT CGACTATTGT TGAGAACCTT
1551 AGGACATACA ATCAGCCTGC CTTTGTCTAC ATTCCCATGG CTGCAGAGCT
1601 ACGAGGAGGG GCTTGGGTTG TGGTTGATAG CAAGATAAAC CCAGACCGCA
1651 TTGAGTGCTA TGCTGAGAGG ACTGCAAAAA GCAATGTTCT GGAACCGCAA
1701 GGGTTAATTG AGATCAAGTT CAGGTCAGAG GAACTCCAGG ATTGCATGAG
1751 TCGGCTTGAC CCAACATTAA TTGATCTGAA AGCAAACTC GAAGTAGCAA
1801 ATAAAAATGG AAGTGCTGAC ACAAAATCGC TTCAAGAAAA TATAGAAGCT
1851 CGAACAAAAC AGTTGATGCC TCTATATACT CAGATTGCGA TACGGTTTGC
1901 TGAATTGCAT GATACATCCC TCAGAATGGC TGCGAAAGGT GTGATTAAGA
1951 AAGTTGTGGA CTGGGAAGAA TCACGATCTT TCTTCTATAA GAGATTACGG
2001 AGGAGGATCT CTGAGGATGT TCTTGCAAAA GAAATTAGAG CTGTAGCAGG
2051 TGAGCAGTTT TCCCACCAAC CAGCAATCGA GCTGATCAAG AAATGGTATT
2101 CAGCTTCACA TGCAGCTGAA TGGGATGATG ACGATGCTTT TGTTGCTTGG
2151 ATGGATAACC CTGAAAACTA CAAGGATTAT ATTCAATATC TTAAGGCTCA
2201 AAGAGTATCC CAATCCCTCT CAAGTCTTTC AGATTCCAGC TCAGATTTGC
2251 AAGCCCTGCC ACAGGGTCTT TCCATGTTAC TAGATAAGGT AATTAGCTTA
2301 CTGATGCTTA TATAAATTCT TTTTCATTAC ATATGGCTGG AGAACTATCT
2351 AATCAAATAA TGATTATAAT TCCAATCGTT CTTTTTATGC CATTATGATC
2401 TTCTGAAATT TCCTTCTTTG GACACTTATT CAGATGGATC CCTCTAGAAG
2451 AGCTCAACTT GTTGAAGAAA TCAGGAAGGT CCTTGGTTGA ATCATATGAT
2501 G
```

FIG. 8

METHODS AND COMPOSITIONS TO PRODUCE RICE RESISTANT TO ACCASE INHIBITORS

This application claims priority from U.S. Provisional Application No. 61/510,585 filed Jul. 22, 2011 and U.S. Provisional Application No. 61/541,832 filed Sep. 30, 2011, both incorporated by reference. Novel rice plants are described and disclosed that are characterized by tolerance/resistance to herbicides that are ACCase inhibitors and exhibit other characteristics beneficial to rice crops. Methods to control weeds by use of herbicide resistant rice in fields, and methods to produce herbicide resistant rice using e.g. transgenes encoding for a mutant ACCase enzyme, are also disclosed.

BACKGROUND

Sequence Listing

The instant application contains a Sequence Listing which has been submitted in ASCII format via EFS-Web and is hereby incorporated by reference in its entirety. Said ASCII copy, created on Jul. 20, 2012, is named 119566_SEQ_ST25.txt and is 32,768 bytes in size.

Value of Rice Crops

Rice is an ancient agricultural crop and is today one of the principal food crops of the world. There are two cultivated species of rice: *Oryza sativa* L., the Asian rice, and *Oryza glaberrima* Steud., the African rice. The Asian species constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is one of the few crops that can be grown in a shallow flood as it has a unique structure allowing gas exchange through the stems between the roots and the atmosphere. Growth in a shallow flood results in the best yields and is the reason that rice is usually gown in heavy clay soils or soils with an impermeable hard pan layer just below the soil surface. These soil types are usually either not suitable for other crops or at the best the crops yield poorly.

The constant improvement of rice is imperative to provide necessary nutrition for a growing world population. A large portion of the world population consumes rice as their primary source of nutrition. Rice improvement is carried out through conventional breeding practices and by recombinant genetic techniques. Though appearing straight forward to those outside this discipline, crop improvement requires keen scientific and artistic skill.

Although specific breeding objectives vary somewhat in the different rice producing regions, increasing yield is a primary objective in all programs.

Plant breeding begins with the analysis and definition of strengths and weaknesses of the current cultivars, followed by the establishment of program goals, to address the latter including the definition of specific breeding objectives. The goal is to combine in a single cultivar an improved combination of desirable traits from the parental sources. These important traits may include higher yield, resistance to environmental stress, diseases and insects, better stems and roots, tolerance to low temperatures, better agronomic characteristics, and grain quality.

The breeder initially selects and crosses two or more parental lines, followed by selection among the many new genetic combinations. The breeder can theoretically generate billions of new and different genetic combinations via crossing. The breeder has no direct control at the cellular level; therefore, two breeders will never develop the same line, or even very similar lines, having the same rice traits.

Pedigree breeding is used commonly for the improvement of self-pollinating crops such as rice. Two parents which possess favorable, complementary traits are crossed to produce an $F_1$ generation. One or both parents may themselves represent an $F_1$ from a previous cross. Subsequently a segregating population is produced, growing the seeds resulting from selfing one or several $F_1$s if the two parents are pure lines, or by directly growing the seed resulting from the initial cross if at least one of the parents is an $F_1$. Selection of the best individuals may begin in the first segregating population or $F_2$; then, beginning in the $F_3$, the best individuals in the best families are selected. "Best" is defined according to the goals of a particular breeding program e.g., to increase yield, resist diseases. Overall a multifactorial approach is used to define "best" because of genetic interactions. A desirable gene in one genetic background may differ in a different background. In addition, introduction of the gene may disrupt other favorable genetic characteristics. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new parental lines.

Backcross breeding has been used to transfer genes for a highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The process is used to recover all of the beneficial characteristics of the recurrent parent with the addition of the new trait provided by the donor parent.

Promising advanced breeding lines are thoroughly tested and compared to appropriate standards in environments representative of the commercial target area(s) for at least three or more years. The best lines are candidates for new commercial varieties or parents of hybrids; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

The improvement of rice through breeding is restricted to the natural genetic variation in rice and hybridizing species, such as wild rice. The introduction of new variation in a breeding program is usually through the crossing program as described, such as pedigree or backcross breeding. However, occasionally natural mutations are found that result in the introduction of new traits such as disease resistance or height changes. Breeders have also developed new traits by inducing mutations (small changes in the DNA sequence) into a rice genome. Commonly, EMS or sodium azide plus MNU are used as mutagenic agents. These chemicals randomly induce single base changes in DNA, usually of G and C changed to A and T. Most of these changes have no effect on the crop as they fall either outside the gene coding regions or don't change the amino acid sequence of the gene product.

The breeder has no direct control of mutation sites in the DNA sequence. The identification of useful changes is due to the random possibility that an effective mutation will be induced and that the breeder will be able to select that mutation. Seeds are treated with the mutagenic chemical and immediately planted to grow and produce M2 seed. The M2 seed will carry numerous new variations; therefore, no two experiments will produce the same combinations. Among these variations new traits previously not existing in rice and unavailable for selection by a plant breeder may be found and used for rice improvement.

To find new traits the breeder must use efficient and strategic selection strategies as the process is completely random and has an extremely low frequency of useful new combinations. Among thousands of induced new genetic variants there may be only one with a desirable new trait. An optimal selection system will screen through thousands of new variants and allow detection of a few or even a single plant that might carry a new trait. After identifying or finding a possible new trait the breeder must develop a new cultivar by pedigree or backcross breeding and extensive testing to verify the new trait and cultivar exhibits stable and heritable value to rice producers.

Using recombinant genetic techniques, nucleic acid molecules with mutations, that encode improved characteristics in rice, may be introduced into rice with commercially suitable genomes. After a mutation is identified, it may be transferred into rice by recombinant techniques.

Applications of Herbicide Resistance Patents in Rice

Weeds in crops compete for resources and greatly reduce the yield and quality of the crop. Weeds have been controlled in crops through the application of selective herbicides that kill the weeds but do not harm the crop. Usually selectivity of the herbicides is based on biochemical variations or differences between the crop and the weeds. Some herbicides are non-selective, meaning they kill all or almost all plants. Non-selective or broad spectrum herbicides can be used in crops if new genes are inserted that express specific proteins that convey tolerance or resistance to the herbicide. Resistance to herbicides has also been achieved in crops through genetic mutations that alter proteins and biochemical processes. These mutations may arise in nature, but mostly they have been induced in crops or in vitro in tissue cultures. Unfortunately in some instances, especially with repeated use of a particular herbicide, weeds have developed resistance through the unintended selection of natural mutations that provide resistance. When weeds become resistant to a particular herbicide, that herbicide is no longer useful for weed control. The development of resistance in weeds is best delayed through alternating the use of different modes of action to control weeds, interrupting development of resistant weeds.

Rice production is plagued by a particularly hard to control weed called red rice. The difficulty arises because red rice is so genetically similar to cultivated rice (they occasionally cross pollinate) that there are no selective herbicides available that target red rice, yet do not harm the cultivated rice. Control is currently provided in commercial rice production through the development of mutations found in rice that render rice resistant to broad spectrum herbicides e.g. imidazolinone and sulfonylurea herbicides.

Finding new mutations in rice that makes it resistant to herbicides, and to combinations of herbicides with alternative modes of action would greatly benefit rice production. Obtaining and incorporating genes for herbicide resistance into rice genomes with additional favorable characteristics and alternative resistances is challenging, unpredictable, time consuming and expensive, but necessary to meet the world's increasing food needs.

SUMMARY

Described herein are distinctive rice lines with unique resistances to herbicides with alternative modes of action. These rice lines should extend the useful life of several herbicides due to being able to rotate the kinds of herbicides applied in grower's fields thus slowing the development of weed resistance. Several methods are possible to deploy these resistances into hybrids or varieties for weed control, as well as options for hybrid seed production. The rice lines described herein represent new methods for weed control in rice and can be deployed in any of many possible strategies to control weeds and provide for long-term use of this and other weed control methods. In particular, mutant rice tolerant to ACCase inhibiting herbicides is disclosed. These are plants with defined amino acid sequences.

For example, rice with the ACCase mutant G2096S is already agronomically adapted and through breeding or backcrossing as described herein, will provide herbicide resistance in commercially suitable biological material.

A mutant rice tolerant to an ACCase inhibitor herbicide is disclosed that has a mutation G2096S in the carboxyl transferase coding region of the ACCase gene, using the Black Grass (*Alopecurus myosuroides*) numbering system. The mutation makes the acetyl-coenzyme A carboxylase enzyme tolerant/resistant to ACCase inhibitors used as herbicides.

Cells derived from herbicide resistant seeds, plants grown from such seeds and cells derived from such plants, progeny of plants grown from such seed and cells derived from such progeny are within the scope of this disclosure. The growth of plants produced from deposited seed, and progeny of such plants will typically be resistant/tolerant to acetyl-Coenzyme A carboxylase-inhibiting herbicides at levels of herbicide that would normally inhibit the growth of a corresponding wild-type plant.

A method for controlling growth of weeds in vicinity to rice plants is also within the scope of the disclosure. One example of such methods is applying one or more herbicides to the weeds and to the rice plants at levels of herbicide that would normally inhibit the growth of a rice plant. For example, at least one herbicide inhibits acetyl-Coenzyme A carboxylase activity. Such methods may be practiced with any herbicide that inhibits acetyl-Coenzyme A carboxylase activity and any resistant rice mutation, e.g., the three embodiments disclosed herein.

A method for growing herbicide-tolerant rice plants include (a) planting resistant rice seeds; (b) allowing the rice seeds to sprout; (c) applying one or more herbicides to the rice sprouts at levels of herbicide that would normally inhibit the growth of a rice plant. For example, at least one of the herbicides inhibits acetyl-Coenzyme A carboxylase. Such methods may be practiced with any herbicide that inhibits acetyl-Coenzyme A carboxylase activity.

Methods of producing herbicide-tolerant rice plants that may also use a transgene. One example of such a method is transforming a cell of a rice plant with a transgene, wherein the transgene encodes an acetyl-Coenzyme A carboxylase enzyme that confers tolerance in resulting rice plant to at least one herbicide selected from the group consisting of aryloxyphenoxypropionate herbicides, cyclohexanedione herbicides, phenypyrazoline herbicides or combinations thereof. Any suitable cell may be used in the practice of these methods, for example, the cell may be in the form of a callus. An embodiment of a transgenic is one comprising a mutation in a nucleic acid encoding ACCase, from G to S in position 2096 (Black Grass numbering system).

A recombinant, mutagenized, synthetic, and/or isolated nucleic acid molecule including a nucleotide sequence encoding a mutagenized acetyl-Coenzyme A carboxylase of a plant rice, in which the amino acid sequence of the mutagenized acetyl-Coenzyme A carboxylase differs from an amino acid sequence of an acetyl-Coenzyme A carboxylase of the corresponding wild-type plant, are within the scope of the disclosure.

Different mutations in the ACCase encoding gene are often associated with resistance to specific types of ACCase inhibiting herbicides (FOPS), (DIMS). The specificity of different mutations thus offers the possibility of developing multiple modes of action for weed control in rice.

BRIEF DESCRIPTION OF DRAWINGS

FIG. 4 shows DNA sequence for the carboxyl transferase coding region in the ACCase coding gene; a single nucleotide change from G2096S is identified in the mutant line ML0831265-01493 which is identified as 09PM72399. FIG. 4 discloses SEQ ID NOS 2-4, respectively, in order of appearance.

FIG. 5 shows comparison of protein sequences for the carboxyl transferase region of the ACCase gene; line with code 09PM72399 is the line ML0831265-01493; this line shows a change of a single amino acid at position 2096, relative to Black-Grass; R0146 is the original line treated with a mutagen to produce the mutation population. FIG. 5 discloses SEQ ID NOS 5-7, respectively, in order of appearance.

FIG. 8 is the mutant nucleotide sequence (SEQ ID NO: 1) that encodes an ACCase enzyme with S instead of G at position 2096 (Black Grass number system).

DETAILED DESCRIPTION

Rice, *Oryza sativa* L., is an important and valuable field crop. Thus, a continuing goal of rice breeders is to develop stable and high yielding rice cultivars that are agronomically sound. Growers are constantly expecting increasing yields from new varieties and hybrids as a way to increase their economic condition. In addition on a population level increasing yields is necessary due to expanding nutritional needs but limited production resources. To accomplish this goal, the rice breeder must select and develop rice plants possessing required traits and superior yields.

Acetyl-Coenzyme A carboxylase (ACCase; EC 6.4.1.2) enzymes synthesize malonyl-CoA as the start of the de novo fatty acid synthesis pathway in plant chloroplasts. ACCase in grass chloroplasts is a multifunctional, nuclear-genome-encoded, very large, single polypeptide, transported into the plastid via an N-terminal transit peptide. The active form in grass chloroplasts is a homodimeric protein.

ACCase enzymes in grasses are inhibited by three classes of herbicidal active ingredients. The two most prevalent classes are aryloxyphenoxypropanoates ("FOPs") and cyclohexanediones ("DIMs"). In addition to these two classes, a third class phenylpyrazolines ("DENs") has been described.

Certain mutations in the carboxyl transferase region of the ACCase enzyme results in grasses becoming resistant to ACCase herbicides. In the weed Black-Grass at least five mutations have been described which provide resistance to FOP or DIM class of ACCase herbicides. Some mutations rendering ACCase enzymes resistant to these herbicides may be associated with decreased fitness.

Mutation Population and Establishment

A mutation breeding program was initiated to develop proprietary herbicide tolerant lines. A permanent mutant population was created by exposing approximately 10,000 seeds (estimated by the average weight of a kernel) of three lines including P1003, R0146, and P1062 to mutagens sodium azide (AZ) and methyl-nitrosourea (MNU). The treated seeds were space planted. Individual plants were harvested creating 8,281 mutation lines. The mutation lines have been maintained as a permanent mutant population for trait screening.

Herbicide Screening

Figure 1:
FIG. 1 shows surviving plants in quizalofop sprayed row 11USAG51477 marked with a flag.
Figure 2:
FIG. 2 shows quizalofop survivors following transplanting.
Figure 3:
FIG. 3 shows a 11USAG52084-2 rice plant with seed set.

The permanent mutant population was screened with quizalofop herbicide. Applicants planted 2,735 M2 progeny rows from R0146, 3,774 M2 progeny rows from P1003 and 655 M2 progeny rows from P1062 in two replications with an estimated 250,000 plants total in each replication. Quizalofop was applied with a rate of 15 oz/acre (115.59 gmai/ha) to the first replication 27 days after planting. Plants were at the 3-4 leaf stage and were actively growing when herbicide was applied. The field was flushed the day after application. After about 9 days surviving plants were found in four different progeny rows showing an estimated mutation rate of 0.006% (FIGS. 1-3).

Protein Sequence Comparison on Lines Showing Resistance to ACCase Herbicides

A portion of the gene that codes for the plastidic ACCase protein was sequenced from all the plants that survived application of quizalofop. Only the carboxyl transferase coding region of the gene was sequenced (FIG. 4). All of the plants deriving from line ML0831265-01493 had a mutation in the DNA sequence that caused an amino acid change in the ACCase protein. One DNA base was changed in the codon for amino acid 2096 relative to numbering in Black-Grass. (Gen Bank CAC84161.1, denoted as "Am") (FIG. 5). In both rice and Black-Grass the amino acid at position 2096 is glycine. A resistant mutation in Black-Grass changes the amino acid at this position to alanine. The mutation found in rice surviving quizalofop application with designation ML0831265-01493 changes the DNA codon for amino acid 2096 from GGC to AGC causing a serine to be inserted in position 2096 instead of glycine. The mutant line showed resistance to quizalofop in the first screening of the mutant population. Later screening with quizalofop confirmed the resistance to FOPs. The surviving mutant lines were susceptible to DIM type ACCase inhibiting herbicides.

None of the other lines from the mutant population that survived screening with quizalofop carried a mutation in the carboxyl transferase region of the ACCase coding gene however they have been confirmed to carry resistance to quizalofop herbicide. The resistance in these lines is likely derived from changes outside the carboxyl transferase region of ACCase or could be derived from a different type of resistant mechanism Resistant Plants After herbicide treatment, the surviving plants before transplanting were green and healthy looking whereas all surrounding plants within the row and in adjacent rows were dead. The plants after transplanting were maintained and harvested. The progeny were maintained, tested, and developed as a source of herbicide resistance in production rice (Table 1). This trait is backcrossed or bred into proprietary rice lines and used to develop new varieties or hybrids that will provide producers with an alternative mode of action to control weeds in rice. Affording this opportunity to growers is of great value both in providing high yields and in extending the useful life of currently used weed control technologies. These herbicide resistant lines can be tracked through the simple application of herbicides to growing plants or through molecular techniques. As the full sequence of the mutation lines is known including the causal mutation for herbicide resistance, molecular markers can be designed, such as single nucleotide polymorphic markers, for the selection of plants and lines carrying the resistance. These markers along with herbicide bioassays facilitate the development of at least FOP type of ACCase herbicide resistance in rice.

Selection of herbicide resistant rice in a breeding program is accomplished by spraying the progeny material with herbicide in a bioassay to observe material inheriting the resistance. Alternatively line ML0831265-01493 may be selected by sequencing the gene region containing the mutation or by creating a single nucleotide polymorphic marker to detect the mutation.

Production of Hybrid Rice Tolerant/Resistant to ACCase Inhibitor

The practical development of the trait for weed control in rice based on the application of ACCase FOP type of herbicides is now possible. Previously these herbicides had no application in rice because they killed the rice plants. Any of the rice lines described is suitable to be developed into a rice cultivar or hybrid and used in rice production as a weed control method. The resistant trait was demonstrated to be fully heritable allowing for breeding and development.

The trait was demonstrated to survive and produce normal seed set after application of FOP herbicides at rates that normally kill rice. In addition the trait was amendable to application with multiple FOP herbicides. The level of herbicide resistance is such to allow complete control of red rice and other grass type weeds.

The trait is fully selectable with either an herbicide bioassay or a molecular marker allowing selection and breeding strategies to develop new rice cultivars and hybrids with FOP herbicide resistance. The resistance provided in line ML0831265-01493 is due to a single gene acting partially dominantly or fully dominantly making it ideally suited to be backcrossed into current commercial cultivars. Alternatively the line ML0831265-01493, though lacking some key quality characteristics for some markets, is still agronomically suitable to be used as a parent line in a pedigree breeding program. Alternatively the line if crossed with certain female lines may be used to directly produce hybrid seed carrying herbicide resistance, as described herein.

Suitable lines that upon conversion with genes disclosed herein produce commercial rice resistant to ACCase inhibiting herbicides rice seeds deposited in the ATCC as PTA-8504, PTA-8505, PTA-836 and PTA-6795. Conversion may be by breeding or recombinant methods.

EXAMPLES

Example 1

Results of Quizalofop Herbicide Rate Response of ML0831265-01493 Plants

Figure 6:
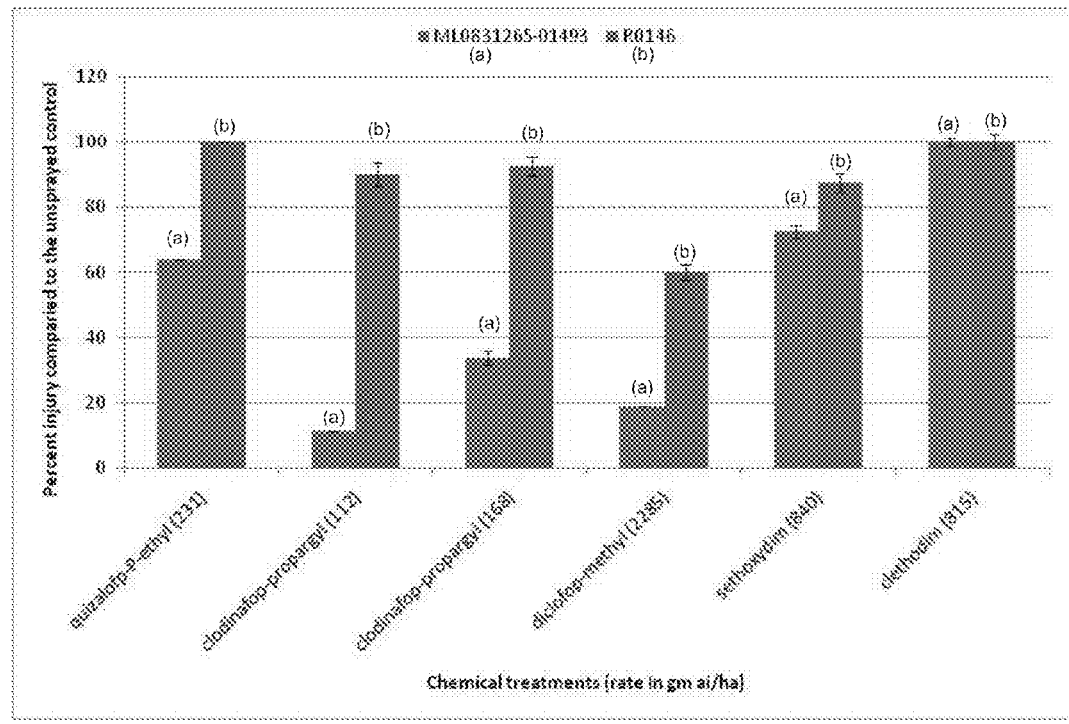
FIG. 6 shows results of plants from ML0831265-01493 at different application rates of quizalofop herbicide.

Rice lines with the G2096S mutation were tested for level of resistance to quizalofop herbicide (Assure II®) by testing a series of different application rates of the herbicide. The herbicide rate treatments were as shown in FIG. 6. All treatments were applied at the 2-3 leaf stage. The plots were evaluated twenty-one days after application. The spray was applied in a volume of 10 gal/acre and with 1% Crop Oil Concentrate. The treatments were evaluated as the percent injury compared to an unsprayed control plot.

The source of the G2096S mutation was line ML0831265-01493. A sample of seed from ML0831265-01493 is deposited with the ATCC. This line is like R0146 except that it has resistance to some ACCase herbicides due to a mutation causing an amino acid change to serine instead of glycine at position 2096 in the ACCase gene.

Four different selections of ML0831265-01493 all with the G2096S mutation were replicated three times in each treatment and tested along with the non-mutant R0146 line. The results are based on scoring twenty-one days after herbicide application.

Example 2

Figure 7:
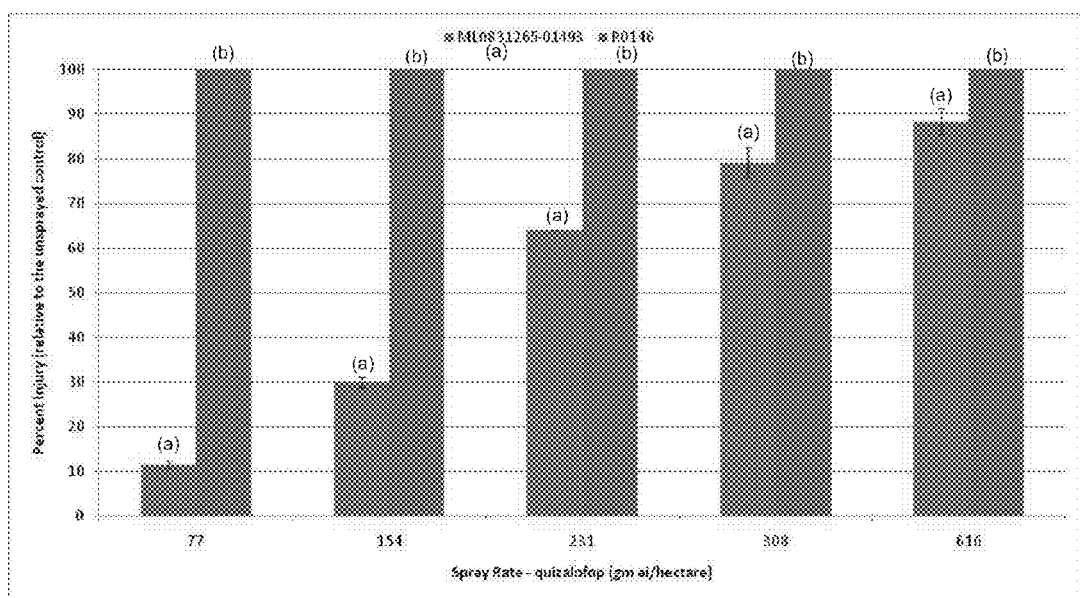
FIG. 7 shows results of plants from ML0831265-01493 with application of different ACCase type herbicides.

Results of ACC Inhibitor Herbicide Rate Response of Rice Lines with the G2096S Mutation Rice lines (ML0831265-01493) with the G2096S mutation were tested for response to different ACCase inhibiting herbicides. A set of herbicides (FIG. 7) were selected and applied to three rice lines with the G2096S mutation along with the non-mutated original variety R0146. The response of R0146 and the mutated line is shown in FIG. 7. The rate of herbicide application is twice the level of the labeled rate except for quizalofop and clethodim, which was twice the rate selected as a rate satisfactory to kill rice.

All treatments were applied at the 2-3 leaf stage about 20 days after seeds were planted. The plots were evaluated twenty-one days after application. The spray was applied in a volume of 10 gal/acre and with 1% Crop Oil Concentrate. The treatments were evaluated as the percent injury compared to an unsprayed control plot.

A sample of seed from ML0831265-01493 is deposited with the ATCC. This line is similar to R0146 except that it has resistance to some ACCase herbicides due to a mutation causing an amino acid change to serine instead of glycine at position 2096 in the ACCase gene.

Three different selections of ML0831265-01493 all with the G2096S mutation were replicated two or three times in each treatment and tested along with the non-mutant R0146 line. The results are based on scoring twenty-one days after herbicide application.

Figure 9:
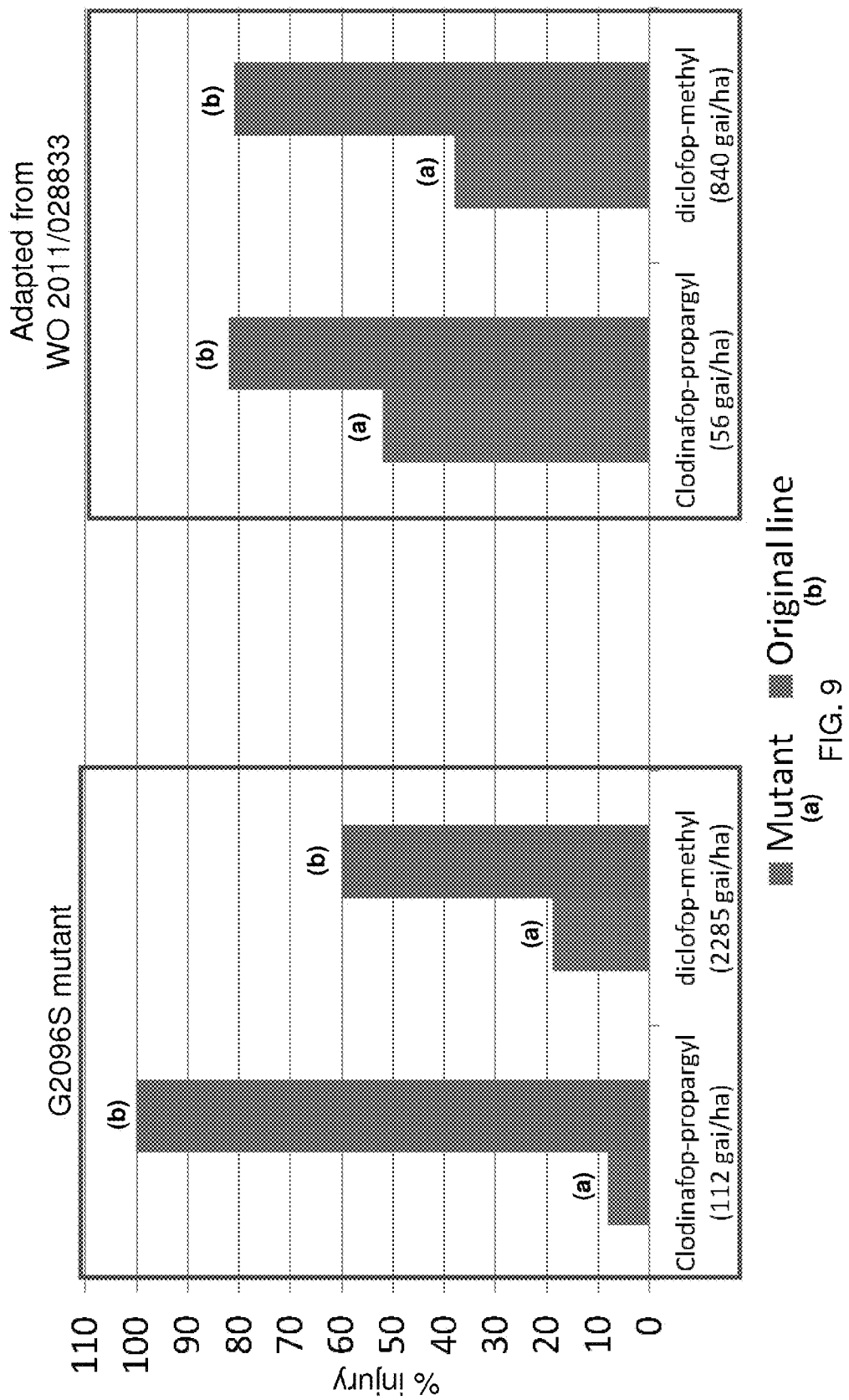
FIG. 9 shows a comparison of % injury after contact with FOP's ACCase inhibiting herbicides in (a) rice plants with a G2096S mutation; and (b) rice plants without the mutation, with a published comparison for a different mutation.

Different mutations in the ACCase encoding gene are often associated with resistance to specific types of ACCase inhibiting herbicides (FOPS), (DIMS). The specificity of different mutations thus offers the possibility of developing multiple modes of action for weed control in rice. For example, FIG. 9 shows that the G2096S mutation disclosed herein conveys greater tolerance in rice to two common FOP type of ACCase inhibiting herbicides than an alternative recently published mutation. The different response of rice line ML0831265-01493 to FOP herbicides shows that commercial development of this line or essentially similar lines provides a new mode of action for weed control not currently available from other sources.

Example 3

Mutant Rice Line ML0831265-01493 Shows No Apparent Differences from Non-Mutated R0146 Rice in Characteristics Other Than ACCase Inhibitor Resistant Rice In research plots the mutant line ML0831265-01493 was observed side by side with the original non-mutant line R0146. No observable differences were identified. The plants showed the same growth pattern. The health and robustness of the plants also appeared similar without any detectable differences. Some characteristics where measured also showed new significant differences between the mutant line ML0831265-01493 and the unmutated line R0146 (Table 2). The G2096S mutation in line ML0831265-01493 shows no negative effects on the normal growth or fitness of the plants.

Example 4

Development of DNA Markers to Select Plants with the Mutation

DNA markers allow selection for certain traits without having to observe the phenotype. In the instance of line ML0831265-01493 the mutation causing the resistance is known including the specific DNA sequence and surrounding sequence. Knowing the sequence allows the design, making, and use of any marker system that will detect single nucleotide polymorphisms.

In most single nucleotide detection assays a primer is labeled with a specific fluorescent dye and synthesized based on the DNA sequence to anneal with one nucleotide at the mutation site. A second primer is also made carrying a second fluorescent dye of a different color to anneal with the alternative nucleotide at the mutation site. Both primers are then allowed to anneal with a sample of DNA from an individual plant. After washing only the primers which have an annealing match remain in the sample. The fluorescence is measured and based on the color detected the nucleotide at the mutation site is determined. A single color indicates the sample was homozygous for either the non-mutant type or the mutant type, depending on the color detected, and detection of both colors indicates the sample was heterozygous.

Applying single nucleotide markers for the mutation allows selection for herbicide resistance without having to observe effects of herbicide application on the plants. Testing by either molecular marker or phenotyping is required until a new line is proven to be homozygous for the mutation. Molecular markers show if a line or plant is homozygous or heterozygous allowing detection of homozygosity one generation earlier than is possible with observing the effect of applying herbicides.

Example 5

Integration of ACCase Resistance into Commercial Lines

Plants are grown from line ML0831265-01493 with the G2096S mutation (donor parent) and plants from the recurrent parent, which in this example is P1233. The P1233 plants are emasculated following standard crossing procedures and pollinated with pollen from plants of line ML0831265-01493. 2-4 inches of leaf material of individual plants are collectively used to make the crosses and to analyze the plants with molecular markers to identify a set of polymorphic markers. It is best to identify approximately 100 polymorphic markers evenly spaced across the rice genome. Harvest F1 seed from the P1233 plants, which was used as the female parent in the cross.

F1 seeds and the recurrent parent line, P1233 are planted and grown again. The F1 seedlings are sprayed with herbicide to verify successful crossing occurred from the herbicide resistant donor parent. Those plants not inheriting resistance will die. In addition the plants could also be tested with a few of the polymorphic markers to verify they were true F1 plants, i.e. received markers from both parents, the crossing process is repeated by using the resistant F1 plants as the male or pollen donor parent to plants from line P1233 emasculated and used as the female parent. After seeds mature the BC1F1 seed is harvested.

The BC1F1 seeds and the recurrent parent line, P1233 are planted and grown. The BC1F1 seedlings are sprayed with herbicide to identify those that inherited the herbicide tolerance mutation from the donor parent. Leaf tissue is collected from tolerant seedlings and submitted to the lab for analysis with polymorphic markers. Five plants are selected that show the highest portion of the line P1233 genome based on the marker analysis. They are used as a pollen donor onto emasculated plants of line P1233. After seeds mature, the BC2F1 seed is harvested.

The BC2F1 and the recurrent parent line, P1233 are planted and grown. The BC2F1 seedlings are sprayed with herbicide to identify those that inherited the herbicide tolerance mutation from the donor parent. Leaf tissue is collected from the tolerant seedlings and submitted to the lab for analysis with all unfixed (segregating) markers. Five plants are selected that show more than 95% recovery of the P1233 genome and these are allowed to self pollinate. The backcrossing step is repeated if no individuals show at least 95% recovery of the P1233 genome. BC2F2 seed is harvested from individual self pollinating plants.

At least 24 individual BC2F2 seeds from each plant are planted and grown. Leaf tissue is collected; DNA is extracted and sequenced to identify individuals that carry the G2096S mutation in homozygous condition. The plants are allowed to self pollinate. The BC2F3 seed from these plants is harvested and identified as a new herbicide tolerant line of P1233. Lines or progeny rows are grown in head rows and selections for the best row are made to advance to hybrid crossing and yield trials.

The same process may also be followed to develop other lines that carry resistance to ACCase FOP type herbicides. The recurrent parent is chosen as an S-line to develop resistance in a female parent used in hybrid production. Alternatively resistance may be developed in more than one recurrent parent. One recurrent parent line is the male line used in a hybrid and the other is the female line used in the hybrid to make a hybrid that carried the resistance (G2096S mutation) in a homozygous condition. Other examples of recurrent parents may be lines carrying current commercial traits such as other herbicide resistances or even transgenic traits. Other parents could be derived from other screenings of mutant lines and selected to combine multiple traits into a single line.

Example 6

Development of New Commercial Lines with Resistance to ACCase Type FOP Herbicides Resistance in rice to ACCase FOP type herbicides is developed in either hybrid parent lines or varieties through a breeding approach. A careful analysis of the line ML0831265-01493 for inherent strengths and weakness is done to identify lines that will correct the weaknesses in line ML0831265-01493. Line ML0831265-01493 carrying the herbicide resistance as the male parent is used so that simple bioassays (spraying the plants with the herbicides and observing those that live as individuals that inherited the resistance) can be applied to verify successful crosses.

After selecting one or more appropriate parents a cross is first made to one selected line. Crosses with other parents could be made in later generations to contribute additional traits or genetic variation. In this example the development process will involve only one cross to P1003 to improve the weak characteristics of the mutant line ML0831265-01493. Other parents are chosen from a mutant population carrying resistance to an alternative herbicide allowing multiple herbicides to be used for weed control in rice production. Parents are also selected that carry an already developed and commercialized herbicide resistance or transgenic trait.

In the first step the selected parent line P1003 is emasculated being used as the female and considered as providing unique characteristics and that when recombined with line ML0831265-01493 will lead towards development of a new variety or parent line for hybrids. Pollen from the mutant line carrying the G2096S mutation ML0831265-01493 is used to pollinate the emasculated plants of line P1003. The F1 seed is harvested and planted. If desired an additional cross could be made to either of the parent lines or to another parent for the purpose of introducing other characteristics and genetic variation.

Growing the F1 seed and applying herbicide is done to verify the cross was successful. The surviving plants should be true F1 and are allowed to self to produce F2 seed. The F2 seed will then be planted and again sprayed to identify plants inheriting the herbicide resistance. The plants remaining alive should be either homozygous or heterozygous for the resistant trait. If other traits are of interest they should also be evaluated at this stage for inheritance in the F2 plants. Select among the F2 plants surviving the herbicide treatment and allow them to self pollinate to produce F3 seed. Harvest F3 seed from individual plants and maintain as an individual F3 family.

The F3 families are then planted as rows and again herbicide applied to identify the F2 plants and F3 families which are homozygous for the herbicide resistance. Selections are made among the F3 families that are homozygous for the herbicide resistance for other traits and characteristics of interest. F4 seed is harvested from the selected rows.

The F4 seed is used directly in yield trials to develop a new variety or test cross to select parents to produce hybrid seed for testing in yield trials. Selections are made among the lines in the yield trials for yield and other target traits and characteristics such as quality. The F4 seed should also be increased to F5 at which selections for target traits can also be made. The F5 seed should be used again in test crosses for yield trials with hybrid seeds as well as being put directly into yield trials if a variety is to be developed.

After yield trials, including multi-location and replicated testing, and full testing of the trait response, a final selection is made to identify one or a few lines to release as a coded line. These lines are then used for seed increase and release as either a new variety or a parent in a hybrid.

Example 7

Herbicide Resistance Deployed in Hybrids

The herbicide resistance described in line ML0831265-01493 is likely either dominant or partially dominant. The resistant event is deployed in a hybrid by being integrated into the male parent, the female parent or both parents. Any combination is developed for successfully controlling weeds in rice with an ACCase FOP type of herbicide. Through following the process of the examples above parent lines are developed to carry the ACCase herbicide resistance. These parent lines are then used in a hybrid seed production system to produce hybrid seed carrying the ACCase resistance to FOP type of herbicides. The seed production process involves planting the female line in rows next to the male lines. The female lines are male sterile so as to prevent self pollination. The female lines then are pollinated by the male lines and harvested to produce F1 seed. The F1 seed is hybrid seed and is planted by growers to produce rice grain. In the situation where a variety is developed, the seed is planted in isolation and then harvested to sell to growers to produce rice grain.

In preparation to produce either hybrid or variety seed from selected lines carrying the ACCase resistance derived from ML0831265-01493 lines must first be purified, extensively tested, and increased.

In the example of producing hybrid seed with resistance to ACCase FOP type of herbicides the resistance may be provided in the male parent, the female parent or both parents. Providing the resistance in both parents could be necessary to have a high enough level of resistance to prevent herbicide damage to the rice when herbicide is applied. However, a more suitable delivery mechanism in hybrids is if the resistance can be provided in either only the female or only the male parent.

By providing the resistance in only the male parent offers a process to eliminate any female selfed seed in a growers field. With resistance being only provided from the male parent then when a grower applies herbicide to his field all of the female selfed plants will be susceptible to the herbicide and thus killed. The grower's field is chemically rogued and results in a pure stand of hybrid plants.

It is also possible to provide ACCase resistance to FOP herbicides through combining with other traits. For example resistance to herbicides with alternative modes of action or other traits such as insect resistance, drought tolerance. Combining with other traits could be either by conventional or transgenic methods.

In one example ACCase resistance is integrated into the female parent and an alternative herbicide resistance is integrated into the male parent. The seed is resistant to both herbicides and a grower may use either or both herbicides for weed control. Alternatively only one type of resistance is delivered in a single hybrid. Both systems as well as other strategies all provide growers with additional options for controlling weeds and will likely extend the useful life of the herbicides. In the case of deploying in only one parent or only one hybrid any red rice that develops resistance through outcrossing will only inherit one type of resistance and will still be controllable through application of an herbicide with an alternative mode of action.

Example 8

Seed Production

The herbicide resistance may be used for production of hybrid seed. As an example, if the female parent is developed with resistance to ACCase FOP type herbicide through inheritance from line ML0831265-01493 then the herbicide could be used in seed production to eliminate the male parent. By deploying into the female parent, making it resistant, then the herbicide is applied to the seed production field to kill the male plants before setting seed but after pollination. In this way the male parent is prevented from setting seed and allows seed production fields to be harvested as a bulk instead of only harvesting the female rows. In addition the purity of hybrid seed may also be verified through deploying the resistances in only one parent. Any selfed seed of the other parent are killed by application of the herbicide.

DEPOSIT INFORMATION

A deposit of the RiceTec, Inc. seeds designated ML0831265-02283 disclosed above and recited in the appended claims has been made with the American Type Culture Collection (ATCC), 10801 University Boulevard, Manassas, Va. 20110. The date of deposit was Mar. 19, 2013. All restrictions will be removed upon granting of a patent, and the deposit is intended to meet all of the requirements of 37 C.F.R. §§1.801-1.809. The ATCC Accession Number is PTA-13619. The deposit will be maintained in the depository for a period of thirty years, or five years after the last request, or for the enforceable life of the patent, whichever is longer, and will be replaced as necessary during that period.

Seeds were deposited on Mar. 19, 2013 under designation ML0831265-02283 as ATCC Accession No. PTA-13619.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

DEFINITIONS

In the description and tables which follow, a number of terms are used. In order to provide a clear and consistent understanding of the specification and claims, including the scope to be given such terms, the following definitions are provided:

Allele. Allele is any one of many alternative forms of a gene, all of which generally relate to one trait or characteristic. In a diploid cell or organism, the two alleles of a given gene occupy corresponding loci on a pair of homologous chromosomes.

Backcrossing. Process of crossing a hybrid progeny to one of the parents, for example, a first generation hybrid F1 with one of the parental genotypes of the F1 hybrid.

Blend. Physically mixing rice seeds of a rice hybrid with seeds of one, two, three, four or more of another rice hybrid, rice variety or rice inbred to produce a crop containing the characteristics of all of the rice seeds and plants in this blend.

Cell. Cell as used herein includes a plant cell, whether isolated, in tissue culture or incorporated in a plant or plant part.

Cultivar. Variety or strain persisting under cultivation.

Embryo. The embryo is the small plant contained within a mature seed.

Essentially all the physiological and morphological characteristics. A plant having essentially all the physiological and morphological characteristics of the hybrid or cultivar, except for the characteristics derived from the converted gene.

Grain Yield. Weight of grain harvested from a given area. Grain yield could also be determined indirectly by multiplying the number of panicles per area, by the number of grains per panicle, and by grain weight.

Locus. A locus is a position on a chromosome occupied by a DNA sequence; it confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Plant. As used herein, the term "plant" includes reference to an immature or mature whole plant, including a plant from which seed or grain or anthers have been removed. Seed or embryo that will produce the plant is also considered to be the plant.

Plant Part. As used herein, the term "plant part" (or a rice plant, or a part thereof) includes protoplasts, leaves, stems, roots, root tips, anthers, seed, grain, embryo, pollen, ovules, cotyledon, hypocotyl, glumes, panicles, flower, shoot, tissue, cells, meristematic cells and the like.

Quantitative Trait Loci (QTL). Genetic loci that controls to some degree numerically measurable traits that are usually continuously distributed.

Regeneration. Regeneration refers to the development of a plant from tissue culture.

Single Gene Converted (Conversion).

Single gene converted (conversion) includes plants developed by a plant breeding technique called backcrossing wherein essentially all of the desired morphological and physiological characteristics of an inbred are recovered, while retaining a single gene transferred into the inbred via crossing and backcrossing. The term can also refer to the introduction of a single gene through genetic engineering techniques known in the art.

TABLE 1

Rice lines derived from the surviving plants in the permanent mutant population confirmed to carry resistance to quizalofop herbicide. The ATCC accession number is shown for the line with the mutation in the carboxyl transferase region of the ACCase gene and one of the other resisitant lines. The ATCC accession number is pending for the other line.

| Designation | ATCC Accession No. | Mutation in CT domain |
| --- | --- | --- |
| ML0831265-01493 | PTA-12933 | G2096S |
| ML0831265-02283 | PTA-13619 | none |
| ML0831265-00776 | pending | none |

TABLE 2

Comparison of the mutant line ML0831265-01493 with the original unmutated line R0146 showing high similarity between the two lines.

| Line/source | Days to 50% Head | Plant Type | height cm | Pubescence | Sheath Color | Awns | Thousand Kernel Weight, g | Yield/plant, g |
|---|---|---|---|---|---|---|---|---|
| R0146 | 87 | Erect | 93 | Pubescent | Green | None | 22.4 | unknown |
| 11AG52084-2 | 88 | Erect | 92 | Pubescent | Green | None | 21.6 | 7.8 g |

The invention claimed is:

1. A method for controlling weeds in a rice field, the method comprising:
   (a) having rice in the field wherein the rice is resistant to ACCase inhibiting herbicides due to a mutation and wherein the rice is produced from rice seeds deposited as ATCC Accession No. PTA-12933 or PTA-13619; and
   (b) applying the herbicides to the field.

2. A method for developing rice with resistance to ACCase inhibiting herbicides, wherein the resistance to ACCase inhibiting herbicides is obtained from the genes of ATCC Accession No. PTA-12933 or PTA-13619, the method comprising
   (a) introgressing rice with genes in seeds deposited as ATCC Accession No. PTA-12933 or PTA-13619 into a non-resistant source of rice; and
   (b) confirming the introgressed rice is resistant by applying at least one of the herbicides and determining that survival is enhanced compared to rice not introgressed.

3. A rice plant designated ML0831265-02283, the plant comprising the genetic information from a representative sample of seed deposited under ATCC Accession No. PTA-13619, that confers resistance to ACCase inhibitors.

4. A rice plant designated ML0831265-01493, the plant comprising the genetic information from a representative sample of seed deposited under ATCC Accession No. PTA-12933, that confers resistance to

SEQUENCE LISTING

<160> NUMBER OF SEQ ID NOS: 7

<210> SEQ ID NO 1
<211> LENGTH: 2501
<212> TYPE: DNA
<213> ORGANISM: Oryza sativa

<400> SEQUENCE: 1

| | | | | | | |
|---|---|---|---|---|---|---|
| cctgttctgc | taggaataat | agaactacat | actgctatga | ttttccactg | gtgagttgac | 60 |
| tgctccctta | tattcaatgc | attaccatag | caaattcata | ttcgttcatg | ttgtcaaaat | 120 |
| aagccgatga | aaattcaaaa | ctgtaggcat | ttgaaactgc | agtgaggaag | tcatggtcct | 180 |
| ctagtacctc | tggtgcttct | aaaggtgttg | aaaatgccca | atgttatgtt | aaagctacag | 240 |
| agttggtatt | tgcggacaaa | catgggtcat | ggggcactcc | tttagttcaa | atggaccggc | 300 |
| ctgctgggct | caatgacatt | ggtatggtag | cttggacctt | gaagatgtcc | actcctgaat | 360 |
| ttcctagtgg | tagggagatt | attgttgttg | caatgatat | tacgttcaga | gctggatcat | 420 |
| ttggcccaag | ggaagatgca | ttttttgaag | ctgttaccaa | cctagcctgt | gagaagaaac | 480 |
| ttcctcttat | ttatttggca | gcaaattctg | gtgctcgaat | tggcatagca | gatgaagtga | 540 |
| aatcttgctt | ccgtgttggg | tggtctgatg | atggcagccc | tgaacgtggg | tttcagtaca | 600 |
| tttatctaag | cgaagaagac | tatgctcgta | ttggcacttc | tgtcatagca | cataagatgc | 660 |
| agctagacag | tggtgaaatt | aggtgggtta | ttgattctgt | tgtgggcaag | gaagatggac | 720 |
| ttggtgtgga | gaatatacat | ggaagtgctg | ctattgccag | tgcttattct | agggcatata | 780 |
| aggagacatt | tacacttaca | tttgtgactg | gaagaactgt | tggaatagga | gcttatcttg | 840 |
| ctcgacttgg | catccggtgc | atacagcgtc | ttgaccagcc | tattattctt | acaggctatt | 900 |
| ctgcactgaa | caagcttctt | gggcgggaag | tgtacagctc | ccacatgcag | ttgggtggtc | 960 |
| ccaaaatcat | ggcaactaat | ggtgttgtcc | atcttactgt | ttcagatgac | cttgaaggcg | 1020 |
| tttctaatat | attgaggtgg | ctcagttatg | ttcctgccta | cattggtgga | ccacttccag | 1080 |
| taacaacacc | gttggaccca | ccggacagac | ctgttgcata | cattcctgag | aactcgtgtg | 1140 |
| atcctcgagc | ggctatccgt | ggtgttgatg | acagccaagg | gaaatggtta | ggtggtatgt | 1200 |
| ttgataaaga | cagctttgtg | gaaacatttg | aaggttgggc | taagacagtg | gttactggca | 1260 |
| gagcaaagct | tggtggaatt | ccagtgggtg | tgatagctgt | ggagactcag | accatgatgc | 1320 |
| aaactatccc | tgctgaccct | ggtcagcttg | attcccgtga | gcaatctgtt | cctcgtgctg | 1380 |
| gacaagtgtg | gtttccagat | tctgcaacca | agactgcgca | ggcattgctg | gacttcaacc | 1440 |
| gtgaaggatt | acctctgttc | atcctcgcta | actggagagg | cttctctggt | ggacaaagag | 1500 |
| atcttttga | aggaattctt | caggctggct | cgactattgt | tgagaacctt | aggacataca | 1560 |
| atcagcctgc | ctttgtctac | attcccatgg | ctgcagagct | acgaggaggg | gcttgggttg | 1620 |
| tggttgatag | caagataaac | ccagaccgca | ttgagtgcta | tgctgagagg | actgcaaaaa | 1680 |
| gcaatgttct | ggaaccgcaa | gggttaattg | agatcaagtt | caggtcagag | gaactccagg | 1740 |
| attgcatgag | tcggcttgac | ccaacattaa | ttgatctgaa | agcaaaactc | gaagtagcaa | 1800 |
| ataaaaatgg | aagtgctgac | acaaaatcgc | ttcaagaaaa | tatagaagct | cgaacaaaac | 1860 |
| agttgatgcc | tctatatact | cagattgcga | tacggtttgc | tgaattgcat | gatacatccc | 1920 |
| tcagaatggc | tgcgaaaggt | gtgattaaga | agttgtgga | ctgggaagaa | tcacgatctt | 1980 |
| tcttctataa | gagattacgg | aggaggatct | ctgaggatgt | tcttgcaaaa | gaaattagag | 2040 |
| ctgtagcagg | tgagcagttt | tcccaccaac | cagcaatcga | gctgatcaag | aaatggtatt | 2100 |

```
cagcttcaca tgcagctgaa tgggatgatg acgatgcttt tgttgcttgg atggataacc      2160
ctgaaaacta aaggattat attcaatatc ttaaggctca aagagtatcc caatccctct       2220
caagtctttc agattccagc tcagatttgc aagccctgcc acagggtctt tccatgttac      2280
tagataaggt aattagctta ctgatgctta tataaattct ttttcattac atatggctgg      2340
agaactatct aatcaaataa tgattataat tccaatcgtt cttttatgc cattatgatc       2400 ttctgaaatt tccttctttg gacacttatt cagatggatc cctctagaag agctcaactt     2460
gttgaagaaa tcaggaaggt ccttggttga atcatatgat g                           2501

<210> SEQ ID NO 2
<211> LENGTH: 2501
<212> TYPE: DNA
<213> ORGANISM: Oryza sativa

<400> SEQUENCE: 2
cctgttctgc taggaataat agaactacat actgctatga ttttccactg gtgagttgac        60
tgctccctta tattcaatgc attaccatag caaattcata ttcgttcatg ttgtcaaaat       120
aagccgatga aaattcaaaa ctgtaggcat ttgaaactgc agtgaggaag tcatggtcct       180
ctagtacctc tggtgcttct aaaggtgttg aaaatgccca atgttatgtt aaagctacag       240
agttggtatt tgcggacaaa catgggtcat ggggcactcc tttagttcaa atggaccggc       300
ctgctgggct caatgacatt ggtatggtag cttggacctt gaagatgtcc actcctgaat       360
ttcctagtgg tagggagatt attgttgttg caatgatat tacgttcaga gctggatcat        420
ttggcccaag ggaagatgca ttttttgaag ctgttaccaa cctagcctgt gagaagaaac       480
ttcctcttat ttatttggca gcaaattctg gtgctcgaat tggcatagca gatgaagtga       540
aatcttgctt ccgtgttggg tggtctgatg atggcagccc tgaacgtggg tttcagtaca       600
tttatctaag cgaagaagac tatgctcgta ttggcacttc tgtcatagca cataagatgc       660
agctagacag tggtgaaatt aggtgggtta ttgattctgt tgtgggcaag gaagatggac       720
ttggtgtgga gaatatacat ggaagtgctg ctattgccag tgcttattct agggcatata       780
aggagacatt tacacttaca tttgtgactg gaagaactgt tggaatagga gcttatcttg       840
ctcgacttgg catccggtgc atacagcgtc ttgaccagcc tattattctt acaggctatt       900
ctgcactgaa caagcttctt gggcgggaag tgtacagctc ccacatgcag ttgggtggtc       960
ccaaaatcat ggcaactaat ggtgttgtcc atcttactgt ttcagatgac cttgaaggcg      1020
tttctaatat attgaggtgg ctcagttatg ttcctgccta cattggtgga ccacttccag      1080
taacaacacc gttggaccca ccggacagac tgttgcata cattcctgag aactcgtgtg       1140
atcctcgagc ggctatccgt ggtgttgatg acagccaagg gaaatggtta ggtggtatgt      1200
ttgataaaga cagctttgtg gaaacatttg aaggttgggc taagacagtg gttactggca      1260
gagcaaagct tggtggaatt ccagtgggtg tgatagctgt ggagactcag accatgatgc      1320
aaactatccc tgctgaccct ggtcagcttg attcccgtga gcaatctgtt cctcgtgctg      1380
gacaagtgtg gtttccagat tctgcaacca agactcgcgca ggcattgctg gacttcaacc     1440
gtgaaggatt acctctgttc atcctcgcta actggagagg cttctctggt ggacaaagag      1500 atcttttga aggaattctt caggctggct cgactattgt tgagaacctt aggacataca       1560
atcagcctgc ctttgtctac attcccatgg ctgcagagct acgaggaggg gcttgggttg      1620
tggttgatag caagataaac ccagaccgca ttgagtgcta tgctgagagg actgcaaaag      1680
```

```
gcaatgttct ggaaccgcaa gggttaattg agatcaagtt caggtcagag gaactccagg    1740
attgcatgag tcggcttgac ccaacattaa ttgatctgaa agcaaaactc gaagtagcaa    1800
ataaaaatgg aagtgctgac acaaaatcgc ttcaagaaaa tatagaagct cgaacaaaac    1860
agttgatgcc tctatatact cagattgcga tacggtttgc tgaattgcat gatacatccc    1920
tcagaatggc tgcgaaaggt gtgattaaga aagttgtgga ctgggaagaa tcacgatctt    1980
tcttctataa gagattacgg aggaggatct ctgaggatgt tcttgcaaaa gaaattagag    2040
ctgtagcagg tgagcagttt tcccaccaac cagcaatcga gctgatcaag aaatggtatt    2100
cagcttcaca tgcagctgaa tgggatgatg acgatgcttt tgttgcttgg atggataacc    2160
ctgaaaacta caaggattat attcaatatc ttaaggctca aagagtatcc caatccctct    2220
caagtctttc agattccagc tcagatttgc aagccctgcc acagggtctt tccatgttac    2280
tagataaggt aattagctta ctgatgctta tataaattct ttttcattac atatggctgg    2340
agaactatct aatcaaataa tgattataat tccaatcgtt cttttttatgc cattatgatc    2400 ttctgaaatt tccttctttg gacacttatt cagatggatc cctctagaag agctcaactt    2460
gttgaagaaa tcaggaaggt ccttggttga atcatatgat g                        2501

<210> SEQ ID NO 3
<211> LENGTH: 2501
<212> TYPE: DNA
<213> ORGANISM: Oryza sativa

<400> SEQUENCE: 3
cctgttctgc taggaataat agaactacat actgctatga ttttccactg gtgagttgac      60
tgctccctta tattcaatgc attaccatag caaattcata ttcgttcatg ttgtcaaaat     120
aagccgatga aaattcaaaa ctgtaggcat ttgaaactgc agtgaggaag tcatggtcct     180
ctagtacctc tggtgcttct aaaggtgttg aaaatgccca atgttatgtt aaagctacag     240
agttggtatt tgcggacaaa catgggtcat ggggcactcc tttagttcaa atggaccggc     300
ctgctgggct caatgacatt ggtatggtag cttggacctt gaagatgtcc actcctgaat     360
ttcctagtgg tagggagatt attgttgttg caaatgatat tacgttcaga gctggatcat     420
ttggcccaag ggaagatgca ttttttgaag ctgttaccaa cctagcctgt gagaagaaac     480
ttcctcttat ttatttggca gcaaattctg gtgctcgaat tggcatagca gatgaagtga     540
atcttgcttt ccgtgttggg tggtctgatg atggcagccc tgaacgtggg tttcagtaca     600
tttatctaag cgaagaagac tatgctcgta ttggcacttc tgtcatagca cataagatgc     660
agctagacag tggtgaaatt aggtgggtta ttgattctgt tgtgggcaag gaagatggac     720
ttggtgtgga gaatatacat ggaagtgctg ctattgccag tgcttattct agggcatata     780
aggagacatt tacacttaca tttgtgactg gaagaactgt tggaatagga gcttatcttg     840
ctcgacttgg catccggtgc atacagcgtc ttgaccagcc tattattctt acaggctatt     900
ctgcactgaa caagcttctt gggcgggaag tgtacagctc ccacatgcag ttgggtggtc     960
ccaaaatcat ggcaactaat ggtgttgtcc atcttactgt tcagatgac cttgaaggcg     1020 tttctaatat attgaggtgg ctcagttatg ttcctgccta cattggtgga ccacttccag    1080
taacaacacc gttggaccca ccggacagac ctgttgcata cattcctgag aactcgtgtg    1140
atcctcgagc ggctatccgt ggtgttgatg acagccaagg gaatggttta ggtggtatgt    1200
ttgataaaga cagctttgtg gaaacatttg aaggttgggc taagacagtg gttactggca    1260
gagcaaagct tggtggaatt ccagtgggtg tgatagctgt ggagactcag accatgatgc    1320
```

```
aaactatccc tgctgaccct ggtcagcttg attcccgtga gcaatctgtt cctcgtgctg   1380
gacaagtgtg gtttccagat tctgcaacca agactgcgca ggcattgctg gacttcaacc   1440
gtgaaggatt acctctgttc atcctcgcta actggagagg cttctctggt ggacaaagag   1500 atcttttttga aggaattctt caggctggct cgactattgt tgagaacctt aggacataca   1560
atcagcctgc ctttgtctac attcccatgg ctgcagagct acgaggaggg gcttgggttg   1620
tggttgatag caagataaac ccagaccgca ttgagtgcta tgctgagagg actgcaaaag   1680
gcaatgttct ggaaccgcaa gggttaattg agatcaagtt caggtcagag gaactccagg   1740
attgcatgag tcggcttgac ccaacattaa ttgatctgaa agcaaaactc gaagtagcaa   1800
ataaaaatgg aagtgctgac acaaaatcgc ttcaagaaaa tatagaagct cgaacaaaac   1860
agttgatgcc tctatatact cagattgcga tacggtttgc tgaattgcat gatacatccc   1920
tcagaatggc tgcgaaaggt gtgattaaga aagttgtgga ctgggaagaa tcacgatctt   1980
tcttctataa agattacggg aggaggatct ctgaggatgt tcttgcaaaa gaaattagag   2040
ctgtagcagg tgagcagttt tcccaccaac cagcaatcga gctgatcaag aaatggtatt   2100
cagcttcaca tgcagctgaa tgggatgatg acgatgcttt tgttgcttgg atggataacc   2160
ctgaaaacta caaggattat attcaatatc ttaaggctca aagagtatcc caatccctct   2220
caagtctttc agattccagc tcagatttgc aagccctgcc acagggtctt tccatgttac   2280
tagataaggt aattagctta ctgatgctta tataaattct ttttcattac atatggctgg   2340
agaactatct aatcaaataa tgattataat tccaatcgtt cttttatgc cattatgatc   2400 ttctgaaatt tccttctttg gacacttatt cagatggatc cctctagaag agctcaactt   2460
gttgaagaaa tcaggaaggt ccttggttga atcatatgat g                      2501

<210> SEQ ID NO 4
<211> LENGTH: 2501
<212> TYPE: DNA
<213> ORGANISM: Oryza sativa

<400> SEQUENCE: 4
cctgttctgc taggaataat agaactacat actgctatga ttttccactg gtgagttgac     60
tgctccctta tattcaatgc attaccatag caaattcata ttcgttcatg ttgtcaaaat    120
aagccgatga aaattcaaaa ctgtaggcat ttgaaactgc agtgaggaag tcatggtcct    180
ctagtacctc tggtgcttct aaaggtgttg aaaatgccca atgttatgtt aaagctacag    240
agttggtatt tgcggacaaa catgggtcat ggggcactcc tttagttcaa atggaccggc    300
ctgctgggct caatgacatt ggtatggtag cttggacctt gaagatgtcc actcctgaat    360
ttcctagtgg tagggagatt attgttgttg caaatgatat tacgttcaga gctggatcat    420
ttggcccaag ggaagatgca ttttttgaag ctgttaccaa cctagcctgt gagaagaaac    480
ttcctcttat ttatttggca gcaaattctg tgtgctcgaat tggcatagca gatgaagtga    540 atcttgctt ccgtgttggg tggtctgatg atggcagccc tgaacgtggg tttcagtaca    600
tttatctaag cgaagaagac tatgctcgta ttggcacttc tgtcatagca cataagatgc    660
agctagacag tggtgaaatt aggtgggtta ttgattctgt tgtgggcaag gaagatggac    720
ttggtgtgga gaatatacat ggaagtgctg ctattgccag tgcttattct agggcatata    780
aggagacatt tacacttaca tttgtgactg gaagaactgt tggaatagga gcttatcttg    840
ctcgacttgg catccggtgc atacagcgtc ttgaccagcc tattattctt acaggctatt    900
```

```
ctgcactgaa caagcttctt gggcgggaag tgtacagctc ccacatgcag ttgggtggtc    960
ccaaaatcat ggcaactaat ggtgttgtcc atcttactgt ttcagatgac cttgaaggcg   1020
tttctaatat attgaggtgg ctcagttatg ttcctgccta cattggtgga ccacttccag   1080
taacaacacc gttggaccca ccggacagac ctgttgcata cattcctgag aactcgtgtg   1140
atcctcgagc ggctatccgt ggtgttgatg acagccaagg gaaatggtta ggtggtatgt   1200
ttgataaaga cagctttgtg gaaacatttg aaggttgggc taagacagtg gttactggca   1260
gagcaaagct tggtggaatt ccagtgggtg tgatagctgt ggagactcag accatgatgc   1320
aaactatccc tgctgaccct ggtcagcttg attcccgtga gcaatctgtt cctcgtgctg   1380
gacaagtgtg gtttccagat tctgcaacca agactgcgca ggcattgctg gacttcaacc   1440
gtgaaggatt acctctgttc atcctcgcta actggagagg cttctctggt ggacaaagag   1500
atctttttga aggaattctt caggctggct cgactattgt tgagaacctt aggacataca   1560
atcagcctgc ctttgtctac attcccatgg ctgcagagct acgaggaggg gcttgggttg   1620
tggttgatag caagataaac ccagaccgca ttgagtgcta tgctgagagg actgcaaaaa   1680
gcaatgttct ggaaccgcaa gggttaattg agatcaagtt caggtcagag gaactccagg   1740
attgcatgag tcggcttgac ccaacattaa ttgatctgaa agcaaaactc gaagtagcaa   1800
ataaaaatgg aagtgctgac acaaaatcgc ttcaagaaaa tatagaagct cgaacaaaac   1860
agttgatgcc tctatatact cagattgcga tacggtttgc tgaattgcat gatacatccc   1920
tcagaatggc tgcgaaaggt gtgattaaga agttgtggga ctgggaagaa tcacgatctt   1980
tcttctataa agattacgg aggaggatct ctgaggatgt tcttgcaaaa gaaattagag   2040
ctgtagcagg tgagcagttt tccccaccaac cagcaatcga gctgatcaag aaatggtatt   2100
cagcttcaca tgcagctgaa tgggatgatg acgatgcttt tgttgcttgg atggataacc   2160
ctgaaaacta caaggattat attcaatatc ttaaggctca aagagtatcc caatccctct   2220
caagtctttc agattccagc tcagatttgc aagccctgcc acagggtctt tccatgttac   2280
tagataaggt aattagctta ctgatgctta tataaattct tttttcattac atatggctgg   2340 agaactatct aatcaaataa tgattataat tccaatcgtt cttttttatgc cattatgatc   2400 ttctgaaatt tccttctttg gacacttatt cagatggatc cctctagaag agctcaactt   2460
gttgaagaaa tcaggaaggt ccttggttga atcatatgat g                        2501
```

<210> SEQ ID NO 5
<211> LENGTH: 674
<212> TYPE: PRT
<213> ORGANISM: Oryza sativa

<400> SEQUENCE: 5

```
Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
    50                  55                  60

Pro Leu Ile Tyr Leu Ala Ala Asn Ser Gly Ala Arg Ile Gly Ile Ala
65                  70                  75                  80

Asp Glu Val Lys Ser Cys Phe Arg Val Gly Trp Ser Asp Asp Gly Ser
                85                  90                  95
```

```
Pro Glu Arg Gly Phe Gln Tyr Ile Tyr Leu Ser Glu Asp Tyr Ala
            100                 105                 110
Arg Ile Gly Thr Ser Val Ile Ala His Lys Met Gln Leu Asp Ser Gly
        115                 120                 125
Glu Ile Arg Trp Val Ile Asp Ser Val Val Gly Lys Glu Asp Gly Leu
    130                 135                 140
Gly Val Glu Asn Ile His Gly Ser Ala Ala Ile Ala Ser Ala Tyr Ser
145                 150                 155                 160
Arg Ala Tyr Lys Glu Thr Phe Thr Leu Thr Phe Val Thr Gly Arg Thr
                165                 170                 175
Val Gly Ile Gly Ala Tyr Leu Ala Arg Leu Gly Ile Arg Cys Ile Gln
            180                 185                 190
Arg Leu Asp Gln Pro Ile Ile Leu Thr Gly Tyr Ser Ala Leu Asn Lys
        195                 200                 205
Leu Leu Gly Arg Glu Val Tyr Ser Ser His Met Gln Leu Gly Gly Pro
210                 215                 220
Lys Ile Met Ala Thr Asn Gly Val Val His Leu Thr Val Ser Asp Asp
225                 230                 235                 240
Leu Glu Gly Val Ser Asn Ile Leu Arg Trp Leu Ser Tyr Val Pro Ala
                245                 250                 255
Tyr Ile Gly Gly Pro Leu Pro Val Thr Thr Pro Leu Asp Pro Pro Asp
            260                 265                 270
Arg Pro Val Ala Tyr Ile Pro Glu Asn Ser Cys Asp Pro Arg Ala Ala
        275                 280                 285
Ile Arg Gly Val Asp Asp Ser Gln Gly Lys Trp Leu Gly Gly Met Phe
290                 295                 300
Asp Lys Asp Ser Phe Val Glu Thr Phe Glu Gly Trp Ala Lys Thr Val
305                 310                 315                 320
Val Thr Gly Arg Ala Lys Leu Gly Gly Ile Pro Val Gly Val Ile Ala
                325                 330                 335
Val Glu Thr Gln Thr Met Met Gln Thr Ile Pro Ala Asp Pro Gly Gln
            340                 345                 350
Leu Asp Ser Arg Glu Gln Ser Val Pro Arg Ala Gly Gln Val Trp Phe
        355                 360                 365
Pro Asp Ser Ala Thr Lys Thr Ala Gln Ala Leu Leu Asp Phe Asn Arg
370                 375                 380
Glu Gly Leu Pro Leu Phe Ile Leu Ala Asn Trp Arg Gly Phe Ser Gly
385                 390                 395                 400
Gly Gln Arg Asp Leu Phe Glu Gly Ile Leu Gln Ala Gly Ser Thr Ile
                405                 410                 415
Val Glu Asn Leu Arg Thr Tyr Asn Gln Pro Ala Phe Val Tyr Ile Pro
            420                 425                 430
Met Ala Ala Glu Leu Arg Gly Gly Ala Trp Val Val Asp Ser Lys
        435                 440                 445
Ile Asn Pro Asp Arg Ile Glu Cys Tyr Ala Glu Arg Thr Ala Lys Gly
        450                 455                 460
Asn Val Leu Glu Pro Gln Gly Leu Ile Glu Ile Lys Phe Arg Ser Glu
465                 470                 475                 480
Glu Leu Gln Asp Cys Met Ser Arg Leu Asp Pro Thr Leu Ile Asp Leu
                485                 490                 495
Lys Ala Lys Leu Glu Val Ala Asn Lys Asn Gly Ser Ala Asp Thr Lys
            500                 505                 510
```

```
Ser Leu Gln Glu Asn Ile Glu Ala Arg Thr Lys Gln Leu Met Pro Leu
            515                 520                 525

Tyr Thr Gln Ile Ala Ile Arg Phe Ala Glu Leu His Asp Thr Ser Leu
        530                 535                 540

Arg Met Ala Ala Lys Gly Val Ile Lys Val Val Asp Trp Glu Glu
545                 550                 555                 560

Ser Arg Ser Phe Phe Tyr Lys Arg Leu Arg Arg Ile Ser Glu Asp
                565                 570                 575

Val Leu Ala Lys Glu Ile Arg Ala Val Ala Gly Glu Gln Phe Ser His
                580                 585                 590

Gln Pro Ala Ile Glu Leu Ile Lys Lys Trp Tyr Ser Ala Ser His Ala
            595                 600                 605

Ala Glu Trp Asp Asp Asp Ala Phe Val Ala Trp Met Asp Asn Pro
        610                 615                 620

Glu Asn Tyr Lys Asp Tyr Ile Gln Tyr Leu Lys Ala Gln Arg Val Ser
625                 630                 635                 640

Gln Ser Leu Ser Ser Leu Ser Asp Ser Ser Asp Leu Gln Ala Leu
                645                 650                 655

Pro Gln Gly Leu Ser Met Leu Leu Asp Lys Val Ile Ser Leu Leu Met
            660                 665                 670

Leu Ile

<210> SEQ ID NO 6
<211> LENGTH: 674
<212> TYPE: PRT
<213> ORGANISM: Oryza sativa

<400> SEQUENCE: 6

Met Asp Arg Pro Ala Gly Leu Asn Asp Ile Gly Met Val Ala Trp Thr
1               5                   10                  15

Leu Lys Met Ser Thr Pro Glu Phe Pro Ser Gly Arg Glu Ile Ile Val
            20                  25                  30

Val Ala Asn Asp Ile Thr Phe Arg Ala Gly Ser Phe Gly Pro Arg Glu
        35                  40                  45

Asp Ala Phe Phe Glu Ala Val Thr Asn Leu Ala Cys Glu Lys Lys Leu
    50                  55                  60

Pro Leu Ile Tyr Leu Ala Ala Asn Ser Gly Ala Arg Ile Gly Ile Ala
65                  70                  75                  80

Asp Glu Val Lys Ser Cys Phe Arg Val Gly Trp Ser Asp Asp Gly Ser
                85                  90                  95

Pro Glu Arg Gly Phe Gln Tyr Ile Tyr Leu Ser Glu Glu Asp Tyr Ala
            100                 105                 110

Arg Ile Gly Thr Ser Val Ile Ala His Lys Met Gln Leu Asp Ser Gly
        115                 120                 125

Glu Ile Arg Trp Val Ile Asp Ser Val Val Gly Lys Glu Asp Gly Leu
    130                 135                 140

Gly Val Glu Asn Ile His Gly Ser Ala Ala Ile Ala Ser Ala Tyr Ser
145                 150                 155                 160

Arg Ala Tyr Lys Glu Thr Phe Thr Leu Thr Phe Val Thr Gly Arg Thr
                165                 170                 175

Val Gly Ile Gly Ala Tyr Leu Ala Arg Leu Gly Ile Arg Cys Ile Gln
            180                 185                 190

Arg Leu Asp Gln Pro Ile Ile Leu Thr Gly Tyr Ser Ala Leu Asn Lys
        195                 200                 205
```

-continued

Leu Leu Gly Arg Glu Val Tyr Ser Ser His Met Gln Leu Gly Gly Pro
210                 215                 220

Lys Ile Met Ala Thr Asn Gly Val Val His Leu Thr Val Ser Asp Asp
225                 230                 235                 240

Leu Glu Gly Val Ser Asn Ile Leu Arg Trp Leu Ser Tyr Val Pro Ala
            245                 250                 255

Tyr Ile Gly Gly Pro Leu Pro Val Thr Thr Pro Leu Asp Pro Pro Asp
            260                 265                 270

Arg Pro Val Ala Tyr Ile Pro Glu Asn Ser Cys Asp Pro Arg Ala Ala
            275                 280                 285

Ile Arg Gly Val Asp Asp Ser Gln Gly Lys Trp Leu Gly Gly Met Phe
290                 295                 300

Asp Lys Asp Ser Phe Val Glu Thr Phe Glu Gly Trp Ala Lys Thr Val
305                 310                 315                 320

Val Thr Gly Arg Ala Lys Leu Gly Gly Ile Pro Val Gly Val Ile Ala
            325                 330                 335

Val Glu Thr Gln Thr Met Met Gln Thr Ile Pro Ala Asp Pro Gly Gln
            340                 345                 350

Leu Asp Ser Arg Glu Gln Ser Val Pro Arg Ala Gly Gln Val Trp Phe
            355                 360                 365

Pro Asp Ser Ala Thr Lys Thr Ala Gln Ala Leu Leu Asp Phe Asn Arg
370                 375                 380

Glu Gly Leu Pro Leu Phe Ile Leu Ala Asn Trp Arg Gly Phe Ser Gly
385                 390                 395                 400

Gly Gln Arg Asp Leu Phe Glu Gly Ile Leu Gln Ala Gly Ser Thr Ile
            405                 410                 415

Val Glu Asn Leu Arg Thr Tyr Asn Gln Pro Ala Phe Val Tyr Ile Pro
            420                 425                 430

Met Ala Ala Glu Leu Arg Gly Gly Ala Trp Val Val Asp Ser Lys
            435                 440                 445

Ile Asn Pro Asp Arg Ile Glu Cys Tyr Ala Glu Arg Thr Ala Lys Gly
450                 455                 460

Asn Val Leu Glu Pro Gln Gly Leu Ile Glu Ile Lys Phe Arg Ser Glu
465                 470                 475                 480

Glu Leu Gln Asp Cys Met Ser Arg Leu Asp Pro Thr Leu Ile Asp Leu
            485                 490                 495

Lys Ala Lys Leu Glu Val Ala Asn Lys Asn Gly Ser Ala Asp Thr Lys
            500                 505                 510

Ser Leu Gln Glu Asn Ile Glu Ala Arg Thr Lys Gln Leu Met Pro Leu
            515                 520                 525

Tyr Thr Gln Ile Ala Ile Arg Phe Ala Glu Leu His Asp Thr Ser Leu
530                 535                 540

Arg Met Ala Ala Lys Gly Val Ile Lys Lys Val Val Asp Trp Glu Glu
545                 550                 555                 560

Ser Arg Ser Phe Phe Tyr Lys Arg Leu Arg Arg Ile Ser Glu Asp
            565                 570                 575

Val Leu Ala Lys Glu Ile Arg Ala Val Ala Gly Glu Gln Phe Ser His
            580                 585                 590

Gln Pro Ala Ile Glu Leu Ile Lys Lys Trp Tyr Ser Ala Ser His Ala
            595                 600                 605

Ala Glu Trp Asp Asp Asp Ala Phe Val Ala Trp Met Asp Asn Pro
610                 615                 620

Glu Asn Tyr Lys Asp Tyr Ile Gln Tyr Leu Lys Ala Gln Arg Val Ser

```
                625                 630                 635                 640
Gln Ser Leu Ser Ser Leu Ser Asp Ser Ser Asp Leu Gln Ala Leu
                    645                 650                 655
Pro Gln Gly Leu Ser Met Leu Leu Asp Lys Val Ile Ser Leu Leu Met
                660                 665                 670
Leu Ile

<210> SEQ ID NO 7
<211> LENGTH: 674
<212> TYPE: PRT
<213> ORGANISM: Oryza sativa

<400> SEQUENCE: 7

Met Asp Arg Pro Ala Gly Leu Asn Asp Ile Gly Met Val Ala Trp Thr
1               5                   10                  15
Leu Lys Met Ser Thr Pro Glu Phe Pro Ser Gly Arg Glu Ile Ile Val
                20                  25                  30
Val Ala Asn Asp Ile Thr Phe Arg Ala Gly Ser Phe Gly Pro Arg Glu
            35                  40                  45
Asp Ala Phe Phe Glu Ala Val Thr Asn Leu Ala Cys Glu Lys Lys Leu
        50                  55                  60
Pro Leu Ile Tyr Leu Ala Ala Asn Ser Gly Ala Arg Ile Gly Ile Ala
65                  70                  75                  80
Asp Glu Val Lys Ser Cys Phe Arg Val Gly Trp Ser Asp Asp Gly Ser
                85                  90                  95
Pro Glu Arg Gly Phe Gln Tyr Ile Tyr Leu Ser Glu Glu Asp Tyr Ala
            100                 105                 110
Arg Ile Gly Thr Ser Val Ile Ala His Lys Met Gln Leu Asp Ser Gly
        115                 120                 125
Glu Ile Arg Trp Val Ile Asp Ser Val Val Gly Lys Glu Asp Gly Leu
130                 135                 140
Gly Val Glu Asn Ile His Gly Ser Ala Ala Ile Ala Ser Ala Tyr Ser
145                 150                 155                 160
Arg Ala Tyr Lys Glu Thr Phe Thr Leu Thr Phe Val Thr Gly Arg Thr
                165                 170                 175
Val Gly Ile Gly Ala Tyr Leu Ala Arg Leu Gly Ile Arg Cys Ile Gln
            180                 185                 190
Arg Leu Asp Gln Pro Ile Ile Leu Thr Gly Tyr Ser Ala Leu Asn Lys
        195                 200                 205
Leu Leu Gly Arg Glu Val Tyr Ser Ser His Met Gln Leu Gly Gly Pro
    210                 215                 220
Lys Ile Met Ala Thr Asn Gly Val Val His Leu Thr Val Ser Asp Asp
225                 230                 235                 240
Leu Glu Gly Val Ser Asn Ile Leu Arg Trp Leu Ser Tyr Val Pro Ala
                245                 250                 255
Tyr Ile Gly Gly Pro Leu Pro Val Thr Thr Pro Leu Asp Pro Pro Asp
            260                 265                 270
Arg Pro Val Ala Tyr Ile Pro Glu Asn Ser Cys Asp Pro Arg Ala Ala
        275                 280                 285
Ile Arg Gly Val Asp Asp Ser Gln Gly Lys Trp Leu Gly Gly Met Phe
    290                 295                 300
Asp Lys Asp Ser Phe Val Glu Thr Phe Glu Gly Trp Ala Lys Thr Val
305                 310                 315                 320
Val Thr Gly Arg Ala Lys Leu Gly Gly Ile Pro Val Gly Val Ile Ala
```

```
                    325                 330                 335
Val Glu Thr Gln Thr Met Met Gln Thr Ile Pro Ala Asp Pro Gly Gln
                340                 345                 350
Leu Asp Ser Arg Glu Gln Ser Val Pro Arg Ala Gly Gln Val Trp Phe
                355                 360                 365
Pro Asp Ser Ala Thr Lys Thr Ala Gln Ala Leu Leu Asp Phe Asn Arg
                370                 375                 380
Glu Gly Leu Pro Leu Phe Ile Leu Ala Asn Trp Arg Gly Phe Ser Gly
385                 390                 395                 400
Gly Gln Arg Asp Leu Phe Glu Gly Ile Leu Gln Ala Gly Ser Thr Ile
                405                 410                 415
Val Glu Asn Leu Arg Thr Tyr Asn Gln Pro Ala Phe Val Tyr Ile Pro
                420                 425                 430
Met Ala Ala Glu Leu Arg Gly Gly Ala Trp Val Val Asp Ser Lys
                435                 440                 445
Ile Asn Pro Asp Arg Ile Glu Cys Tyr Ala Glu Arg Thr Ala Lys Ser
450                 455                 460
Asn Val Leu Glu Pro Gln Gly Leu Ile Glu Ile Lys Phe Arg Ser Glu
465                 470                 475                 480
Glu Leu Gln Asp Cys Met Ser Arg Leu Asp Pro Thr Leu Ile Asp Leu
                485                 490                 495
Lys Ala Lys Leu Glu Val Ala Asn Lys Asn Gly Ser Ala Asp Thr Lys
                500                 505                 510
Ser Leu Gln Glu Asn Ile Glu Ala Arg Thr Lys Gln Leu Met Pro Leu
                515                 520                 525
Tyr Thr Gln Ile Ala Ile Arg Phe Ala Glu Leu His Asp Thr Ser Leu
                530                 535                 540
Arg Met Ala Ala Lys Gly Val Ile Lys Lys Val Val Asp Trp Glu Glu
545                 550                 555                 560
Ser Arg Ser Phe Phe Tyr Lys Arg Leu Arg Arg Arg Ile Ser Glu Asp
                565                 570                 575
Val Leu Ala Lys Glu Ile Arg Ala Val Ala Gly Glu Gln Phe Ser His
                580                 585                 590
Gln Pro Ala Ile Glu Leu Ile Lys Lys Trp Tyr Ser Ala Ser His Ala
                595                 600                 605
Ala Glu Trp Asp Asp Asp Ala Phe Val Ala Trp Met Asp Asn Pro
                610                 615                 620
Glu Asn Tyr Lys Asp Tyr Ile Gln Tyr Leu Lys Ala Gln Arg Val Ser
625                 630                 635                 640
Gln Ser Leu Ser Ser Leu Ser Asp Ser Ser Asp Leu Gln Ala Leu
                645                 650                 655
Pro Gln Gly Leu Ser Met Leu Leu Asp Lys Val Ile Ser Leu Leu Met
                660                 665                 670
Leu Ile
```